(12) United States Patent
Oh et al.

(10) Patent No.: US 12,679,875 B2
(45) Date of Patent: Jul. 14, 2026

(54) HUMAN EPIDERMAL GROWTH FACTOR-TF FUSION PROTEIN AND USE THEREOF

(71) Applicant: KOREA INSTITUTE OF OCEAN SCIENCE & TECHNOLOGY, Busan (KR)

(72) Inventors: Chul Hong Oh, Jeju-si (KR); Yoon Hyeok Kang, Jeju-si (KR); Eun Young Jo, Jeju-si (KR); Do Hyung Kang, Jeju-si (KR); Young Deuk Lee, Jeju-si (KR); Duck Hee Jang, Busan (KR); Ye Hui Gang, Jeju-si (KR); Tae Yang Eom, Jeju-si (KR); Sachithra Amarin Hettiarachchi, Jeju-si (KR)

(73) Assignee: KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 1028 days.

(21) Appl. No.: 17/774,745

(22) PCT Filed: Nov. 6, 2020

(86) PCT No.: PCT/KR2020/015508
§ 371 (c)(1),
(2) Date: Oct. 3, 2022

(87) PCT Pub. No.: WO2021/091304
PCT Pub. Date: May 14, 2021

(65) Prior Publication Data
US 2023/0032072 A1     Feb. 2, 2023

(30) Foreign Application Priority Data

Nov. 8, 2019 (KR) ......................... 10-2019-0142493
Nov. 5, 2020 (KR) ......................... 10-2020-0147113

(51) Int. Cl.
| | |
|---|---|
| *C07K 14/485* | (2006.01) |
| *A61K 8/64* | (2006.01) |
| *A61K 38/00* | (2006.01) |
| *A61P 17/02* | (2006.01) |
| *A61Q 19/00* | (2006.01) |
| *C07K 14/245* | (2006.01) |
| *C12N 9/24* | (2006.01) |

(52) U.S. Cl.
CPC .............. *C07K 14/485* (2013.01); *A61K 8/64* (2013.01); *A61P 17/02* (2018.01); *A61Q 19/00* (2013.01); *C07K 14/245* (2013.01); *C12N 9/248* (2013.01); *A61K 38/00* (2013.01); *C07K 2319/02* (2013.01)

(58) Field of Classification Search
CPC .............. C07K 14/485; C07K 14/245; C07K 2319/02; A61P 17/02; A61K 8/64; A61K 38/00; A61Q 19/00; C12N 9/248
See application file for complete search history.

(56) References Cited

U.S. PATENT DOCUMENTS

| | | | |
|---|---|---|---|
| 9,963,484 B2 | 5/2018 | Lee et al. | |
| 10,118,956 B2 * | 11/2018 | Retallack | ....... C12Y 304/21009 |
| 2009/0155277 A1 * | 6/2009 | Odani | ..................... A61P 11/02 |
| | | | 424/139.1 |

FOREIGN PATENT DOCUMENTS

| | | | | |
|---|---|---|---|---|
| JP | 2009203181 A | 9/2009 | | |
| KR | 10-2010-0042305 A | 4/2010 | | |
| WO | WO-2006056483 A1 * | 6/2006 | ........... | C07K 14/585 |
| WO | 2009031852 A2 | 3/2009 | | |
| WO | WO-2014172631 A2 * | 10/2014 | ............... | C12N 9/90 |
| WO | WO-2019060574 A1 * | 3/2019 | ............... | C12N 9/88 |

OTHER PUBLICATIONS

Kang et al., Large Quantities Secretion to Culture Medium with Epidermal Growth Factor and Trigger Factor Fused Protein in *Escherichia coli*, New Approaches and Concepts in Microbiology, published Jul. 7, 2019, p. 155. (Year: 2019).*
Gong et al., GenBank Accession No. AFG28235.1, "XynA, partial [Bacillus subtilis]," published 2012.; (Year: 2012).*
Chichili et al., Linkers in the structural biology of protein-protein interactions, Protein Science, published 2013, vol. 22, No. 2, p. 153-167 (Year: 2013).*
Makowska et al., Influence of the Length of the Alanine Spacer on the Acidic-Basic Properties of the Ac-Lys-(Ala)n-Lys-NH2 Peptides (n 5 0, 1, 2, . . . , 5), J Solution Chem, published Oct. 13, 2012, vol. 41, p. 1738-1746 (Year: 2012).*

(Continued)

*Primary Examiner* — David Steadman
*Assistant Examiner* — Scott E. Mulder
(74) *Attorney, Agent, or Firm* — MEDLER FERRO WOODHOUSE & MILLS PLLC

(57) ABSTRACT

The present invention relates to a novel human epidermal growth factor (hEGF)-trigger factor (TF) fusion protein and a use thereof. More particularly, the human epidermal growth factor (hEGF)-trigger factor (TF) fusion protein of the present invention has fused therein: a signal peptide of a *Bacillus subtilis*-derived xylanase; a human epidermal growth factor (hEGF); and an *Escherichia coli*-derived trigger factor (TF). Therefore, the present invention not only enhances the water solubility and expression rate of a target protein, but also notably enhances useful effects such as the effects of increasing skin cell growth and healing a wound, and thus may be widely used in various industries as an active ingredient for a functional cosmetic composition and a pharmaceutical composition.

7 Claims, 6 Drawing Sheets
Specification includes a Sequence Listing.

(56)         References Cited

OTHER PUBLICATIONS

Bui et al., "mRNA Engineering for the Efficient Chaperone-Mediated Co-Translational Folding of Recombinant Proteins in *Escherichia coli*," Int J Mol Sci, 20(13):3163 (2019).
GenBank Accession No. AAS83395.1, "epidermal growth factor, partial [*Homo sapiens*]," 2016.
GenBank Accession No. AFG28235.1, "XynA, partial [Bacillus subtilis]," 2012.
GenBank Accession No. WP_097513460.1, "trigger factor [*Escherichia coli*]," 2019.
Kang et al., "Large Quantities Secretion to Culture Medium with Epidermal Growth Factor and Trigger Factor Fused Protein in *Escherichia coli*," Abstract. New Approaches and Concepts in Microbiology. 2019. p. 155.
Oh et al., "Production of Functional Proteins by Using Secretory Signal Peptide of Marine Bacteria Origin," Abstract. The 12th KSMB Annual Meeting and Symposium. 2016. p. 207.

* cited by examiner hEGF-TF(A):

ATG                                                                                                    TAA hEGF-TF(B):

ATG                                                                                                    TAA

SEQUENCE LISTING

```
<160> NUMBER OF SEQ ID NOS: 11

<210> SEQ ID NO 1
<211> LENGTH: 84
<212> TYPE: DNA
<213> ORGANISM: Artificial Sequence
<220> FEATURE:
<223> OTHER INFORMATION: Bacillus subtilis xylanase signal peptide
      nucleotide

<400> SEQUENCE: 1
atgtttaagt ttaaaaagaa tttcttagtt ggattatcgg cagctttaat gagtattagc        60 ttgtttttcgg caaccgcctc tgct        84

<210> SEQ ID NO 2
<211> LENGTH: 84
<212> TYPE: DNA
<213> ORGANISM: Artificial Sequence
<220> FEATURE:
<223> OTHER INFORMATION: codon-optimized signal peptide nucleotide

<400> SEQUENCE: 2
atgttcaaat tcaaaaaaaa cttcctggtc ggattgtcag cagccttgat gtctatctcg        60 cttttttagtg caacagcttc ggca        84

<210> SEQ ID NO 3
<211> LENGTH: 159
<212> TYPE: DNA
<213> ORGANISM: Artificial Sequence
<220> FEATURE:
<223> OTHER INFORMATION: human EGF nucleotide

<400> SEQUENCE: 3
```

```
aatagtgact ctgaatgtcc cctgtcccac gatgggtact gcctccatga tggtgtgtgc        60
atgtatattg aagcattgga caagtatgca tgcaactgtg ttgttggcta catcgggagg       120
cgatgtcagt accgagacct gaagtggtgg gaactgcgc                              159

<210> SEQ ID NO 4
<211> LENGTH: 162
<212> TYPE: DNA
<213> ORGANISM: Artificial Sequence
<220> FEATURE:
<223> OTHER INFORMATION: codon-optimized human EGF nucleotide

<400> SEQUENCE: 4
gccaattcag attcggagtg tccattatca cacgatggtt attgtttaca tgatgggtg        60 tgtatgtaca ttgaggcgtt agacaaatac gcttgtaatt gtgtggtcgg ctacattggg       120
gagcgttgcc agtaccgtga cttaaagtgg tgggagcttc gc                         162

<210> SEQ ID NO 5
<211> LENGTH: 1299
<212> TYPE: DNA
<213> ORGANISM: Artificial Sequence
<220> FEATURE:
<223> OTHER INFORMATION: TF nucleotide

<400> SEQUENCE: 5
atgcaagttt cagttgaaac cactcaaggc cttggccgcc gtgtaacgat tactatcgct        60
gctgacagca tcgagaccgc tgttaaaagc gagctggtca acgttgcgaa aaaagtacgt       120
attgacggct tccgcaaagg caaagtgcca atgaatatcg ttgctcagcg ttatggcgcg       180
tctgtacgcc aggacgttct gggtgacctg atgagccgta acttcattga cgccatcatt       240
aaagaaaaaa tcaatccggc tggcgcaccg acttatgttc cgggcgaata caagctgggt       300
gaagacttca cttactctgt agagtttgaa gtttatccgg aagttgaact gcagggtctg       360
gaagcgatcg aagttgaaaa accgatcgtt gaagtgaccg acgctgacgt tgacggcatg       420
ctggatactc tgcgtaaaca gcaggcgacc tggaaagaaa aagacggcgc tgttgaagca       480
gaagaccgcg taaccatcga cttcaccggt tctgtagacg gcgaagagtt cgaaggcggt       540
aaagcgtctg atttcgtact ggcgatgggc caggtcgta tgatcccggg ctttgaagac       600
ggtatcaaag ccacaaagc tggcgaagag ttcaccatcg acgtgacctt cccgaagaa       660 taccacgcag aaaacctgaa aggtaaagca gcgaaattcg ctatcaacct gaagaaagtt       720
gaagagcgtg aactgccgga actgactgca gaattcatca acgtttcgg cgttgaagat       780 ggttccgtag aaggtctgcg cgctgaagtg cgtaaaaaca tggagcgcga gctgaagagc       840
gccatccgta accgcgttaa gtctcaggcg atcgaaggtc tggtaaaagc taacgacatc       900
gacgtaccgg ctgcgctgat cgacagcgaa atcgacgttc tgcgtcgcca ggctgcacag       960
cgtttcggtg gcaacgaaaa acaagctctg gaactgccgc gcgaactgtt cgaagaacag      1020
gctaaacgcc gcgtagttgt tggcctgctg ctgggcgaag ttatccgcac caacgagctg      1080
aaagctgacg aagagcgcgt gaaaggcctg atcgaagaga tggcttctgc gtacgaagat      1140
ccgaaagaag ttatcgagtt ctacagcaaa aacaaagaac tgatggacaa catgcgcaat      1200
gttgctctgg aagaacaggc tgttgaagct gtactggcga aagcgaaagt gactgaaaaa      1260
gaaaccactt tcaacgagct gatgaaccag caggcgtaa                            1299

<210> SEQ ID NO 6
```

-continued

```
<211> LENGTH: 1545
<212> TYPE: DNA
<213> ORGANISM: Artificial Sequence
<220> FEATURE:
<223> OTHER INFORMATION: hEGF-TF(A) nucleotide

<400> SEQUENCE: 6
atgttcaaat tcaaaaaaaa cttcctggtc ggattgtcag cagccttgat gtctatctcg        60 cttttttagtg caacagcttc ggcagccaat tcagattcgg agtgtccatt atcacacgat       120
ggttattgtt tacatgatgg ggtgtgtatg tacattgagg cgttagacaa atacgcttgt       180
aattgtgtgg tcggctacat tggggagcgt tgccagtacc gtgacttaaa gtggtgggag       240
cttcgcatgc aagtttcagt tgaaaccact caaggccttg ccgccgtgt aacgattact        300 atcgctgctg acagcatcga gaccgctgtt aaaagcgagc tggtcaacgt tgcgaaaaaa       360
gtacgtattg acggcttccg caaaggcaaa gtgccaatga atatcgttgc tcagcgttat      420
ggcgcgtctg tacgccagga cgttctgggt gacctgatga gccgtaactt cattgacgcc      480
atcattaaag aaaaaatcaa tccggctggc gcaccgactt atgttccggg cgaatacaag      540
ctgggtgaag acttcactta ctctgtagag tttgaagttt atccggaagt tgaactgcag      600
ggtctggaag cgatcgaagt tgaaaaaccg atcgttgaag tgaccgacgc tgacgttgac      660
ggcatgctgg atactctgcg taaacagcag gcgacctgga agaaaaaga cggcgctgtt        720 gaagcagaag accgcgtaac catcgacttc accggttctg tagacggcga gagttcgaa        780 ggcggtaaag cgtctgattt cgtactggcg atgggccagg tcgtatgat cccgggcttt       840 gaagacggta tcaaaggcca caaagctggc gaagagttca ccatcgacgt gaccttcccg      900
gaagaatacc acgcagaaaa cctgaaaggt aaagcagcga aattcgctat caacctgaag      960
aaagttgaag agcgtgaact gccggaactg actgcagaat tcatcaaacg tttcggcgtt     1020
gaagatggtt ccgtagaagg tctgcgcgct gaagtgcgta aaaacatgga gcgcgagctg     1080
aagagcgcca tccgtaaccg cgttaagtct caggcgatcg aaggtctggt aaaagctaac     1140
gacatcgacg taccggctgc gctgatcgac agcgaaatcg acgttctgcg tcgccaggct     1200
gcacagcgtt tcggtggcaa cgaaaaacaa gctctggaac tgccgcgcga actgttcgaa     1260
gaacaggcta aacgccgcgt agttgttggc ctgctgctgg gcgaagttat ccgcaccaac     1320
gagctgaaag ctgacgaaga gcgcgtgaaa ggcctgatcg aagagatggc ttctgcgtac    1380
gaagatccga agaagttat cgagttctac agcaaaaaca aagaactgat ggacaacatg    1440
cgcaatgttg ctctggaaga acaggctgtt gaagctgtac tggcgaaagc gaaagtgact    1500
gaaaaagaaa ccactttcaa cgagctgatg aaccagcagg cgtaa                     1545

<210> SEQ ID NO 7
<211> LENGTH: 1547
<212> TYPE: DNA
<213> ORGANISM: Artificial Sequence
<220> FEATURE:
<223> OTHER INFORMATION: hEGF-TF(B) nucleotide

<400> SEQUENCE: 7
atgttcaaat tcaaaaaaaa cttcctggtc ggattgtcag cagccttgat gtctatctcg        60 cttttttagtg caacagcttc ggcagccaat tcagattcgg agtgtccatt atcacacgat       120
ggttattgtt tacatgatgg ggtgtgtatg tacattgagg cgttagacaa atacgcttgt       180
aattgtgtgg tcggctacat tggggagcgt tgccagtacc gtgacttaaa gtggtgggag       240
cttcgctaat gcaagtttca gttgaaacca ctcaaggcct tggccgccgt gtaacgatta      300
```

-continued

```
ctatcgctgc tgacagcatc gagaccgctg ttaaaagcga gctggtcaac gttgcgaaaa    360
aagtacgtat tgacggcttc cgcaaaggca aagtgccaat gaatatcgtt gctcagcgtt    420
atggcgcgtc tgtacgccag gacgttctgg gtgacctgat gagccgtaac ttcattgacg    480
ccatcattaa agaaaaaatc aatccggctg gcgcaccgac ttatgttccg ggcgaataca    540
agctgggtga agacttcact tactctgtag agtttgaagt ttatccggaa gttgaactgc    600
agggtctgga agcgatcgaa gttgaaaaac cgatcgttga agtgaccgac gctgacgttg    660
acggcatgct ggatactctg cgtaaacagc aggcgacctg gaaagaaaaa gacggcgctg    720
ttgaagcaga gaccgcgta accatcgact tcaccggttc tgtagacggc gaagagttcg    780
aaggcggtaa agcgtctgat ttcgtactgg cgatgggcca gggtcgtatg atcccgggct    840
ttgaagacgg tatcaaaggc cacaaagctg gcgaagagtt caccatcgac gtgaccttcc    900
cggaagaata ccacgcagaa aacctgaaag gtaaagcagc gaaattcgct atcaacctga    960
agaaagttga gagcgtgaa ctgccggaac tgactgcaga attcatcaaa cgtttcggcg    1020
ttgaagatgg ttccgtagaa ggtctgcgcg ctgaagtgcg taaaaacatg gagcgcgagc    1080
tgaagagcgc catccgtaac cgcgttaagt ctcaggcgat cgaaggtctg gtaaaagcta    1140
acgacatcga cgtaccggct gcgctgatcg acagcgaaat cgacgttctg cgtcgccagg    1200
ctgcacagcg tttcggtggc aacgaaaaac aagctctgga actgccgcgc gaactgttcg    1260
aagaacaggc taaacgccgc gtagttgttg gcctgctgct gggcgaagtt atccgcacca    1320
acgagctgaa agctgacgaa gagcgcgtga aaggcctgat cgaagagatg gcttctgcgt    1380
acgaagatcc gaaagaagtt atcgagttct acagcaaaaa caaagaactg atggacaaca    1440
tgcgcaatgt tgctctggaa gaacaggctg ttgaagctgt actggcgaaa gcgaaagtga    1500
ctgaaaaaga aaccactttc aacgagctga tgaaccagca ggcgtaa    1547
```

```
<210> SEQ ID NO 8
<211> LENGTH: 28
<212> TYPE: PRT
<213> ORGANISM: Artificial Sequence
<220> FEATURE:
<223> OTHER INFORMATION: SP protein

<400> SEQUENCE: 8

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala
            20                  25

<210> SEQ ID NO 9
<211> LENGTH: 53
<212> TYPE: PRT
<213> ORGANISM: Artificial Sequence
<220> FEATURE:
<223> OTHER INFORMATION: human EGF protein

<400> SEQUENCE: 9

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
```

-continued

50

```
<210> SEQ ID NO 10
<211> LENGTH: 432
<212> TYPE: PRT
<213> ORGANISM: Artificial Sequence
<220> FEATURE:
<223> OTHER INFORMATION: TF protein

<400> SEQUENCE: 10

Met Gln Val Ser Val Glu Thr Thr Gln Gly Leu Gly Arg Arg Val Thr
1               5                   10                  15

Ile Thr Ile Ala Ala Asp Ser Ile Glu Thr Ala Val Lys Ser Glu Leu
            20                  25                  30

Val Asn Val Ala Lys Lys Val Arg Ile Asp Gly Phe Arg Lys Gly Lys
        35                  40                  45

Val Pro Met Asn Ile Val Ala Gln Arg Tyr Gly Ala Ser Val Arg Gln
    50                  55                  60

Asp Val Leu Gly Asp Leu Met Ser Arg Asn Phe Ile Asp Ala Ile Ile
65                  70                  75                  80

Lys Glu Lys Ile Asn Pro Ala Gly Ala Pro Thr Tyr Val Pro Gly Glu
                85                  90                  95

Tyr Lys Leu Gly Glu Asp Phe Thr Tyr Ser Val Glu Phe Glu Val Tyr
            100                 105                 110

Pro Glu Val Glu Leu Gln Gly Leu Glu Ala Ile Glu Val Glu Lys Pro
            115                 120                 125

Ile Val Glu Val Thr Asp Ala Asp Val Asp Gly Met Leu Asp Thr Leu
    130                 135                 140

Arg Lys Gln Gln Ala Thr Trp Lys Glu Lys Asp Gly Ala Val Glu Ala
145                 150                 155                 160

Glu Asp Arg Val Thr Ile Asp Phe Thr Gly Ser Val Asp Gly Glu Glu
                165                 170                 175

Phe Glu Gly Gly Lys Ala Ser Asp Phe Val Leu Ala Met Gly Gln Gly
            180                 185                 190

Arg Met Ile Pro Gly Phe Glu Asp Gly Ile Lys Gly His Lys Ala Gly
            195                 200                 205

Glu Glu Phe Thr Ile Asp Val Thr Phe Pro Glu Glu Tyr His Ala Glu
    210                 215                 220

Asn Leu Lys Gly Lys Ala Ala Lys Phe Ala Ile Asn Leu Lys Lys Val
225                 230                 235                 240

Glu Glu Arg Glu Leu Pro Glu Leu Thr Ala Glu Phe Ile Lys Arg Phe
                245                 250                 255

Gly Val Glu Asp Gly Ser Val Glu Gly Leu Arg Ala Glu Val Arg Lys
            260                 265                 270

Asn Met Glu Arg Glu Leu Lys Ser Ala Ile Arg Asn Arg Val Lys Ser
            275                 280                 285

Gln Ala Ile Glu Gly Leu Val Lys Ala Asn Asp Ile Asp Val Pro Ala
    290                 295                 300

Ala Leu Ile Asp Ser Glu Ile Asp Val Leu Arg Arg Gln Ala Ala Gln
305                 310                 315                 320

Arg Phe Gly Gly Asn Glu Lys Gln Ala Leu Glu Leu Pro Arg Glu Leu
                325                 330                 335

Phe Glu Glu Gln Ala Lys Arg Arg Val Val Val Gly Leu Leu Leu Gly
            340                 345                 350

Glu Val Ile Arg Thr Asn Glu Leu Lys Ala Asp Glu Glu Arg Val Lys
```

```
              355                 360                 365

Gly Leu Ile Glu Glu Met Ala Ser Ala Tyr Glu Asp Pro Lys Glu Val
        370                 375                 380

Ile Glu Phe Tyr Ser Lys Asn Lys Glu Leu Met Asp Asn Met Arg Asn
385                 390                 395                 400

Val Ala Leu Glu Glu Gln Ala Val Glu Ala Val Leu Ala Lys Ala Lys
                405                 410                 415

Val Thr Glu Lys Glu Thr Thr Phe Asn Glu Leu Met Asn Gln Gln Ala
            420                 425                 430

<210> SEQ ID NO 11
<211> LENGTH: 514
<212> TYPE: PRT
<213> ORGANISM: Artificial Sequence
<220> FEATURE:
<223> OTHER INFORMATION: hEGF-TF protein

<400> SEQUENCE: 11

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Asn Ser Asp
            20                  25                  30

Ser Glu Cys Pro Leu Ser His Asp Gly Tyr Cys Leu His Asp Gly Val
        35                  40                  45

Cys Met Tyr Ile Glu Ala Leu Asp Lys Tyr Ala Cys Asn Cys Val Val
        50                  55                  60

Gly Tyr Ile Gly Glu Arg Cys Gln Tyr Arg Asp Leu Lys Trp Trp Glu
65                  70                  75                  80

Leu Arg Met Gln Val Ser Val Glu Thr Thr Gln Gly Leu Gly Arg Arg
                85                  90                  95

Val Thr Ile Thr Ile Ala Ala Asp Ser Ile Glu Thr Ala Val Lys Ser
            100                 105                 110

Glu Leu Val Asn Val Ala Lys Lys Val Arg Ile Asp Gly Phe Arg Lys
        115                 120                 125

Gly Lys Val Pro Met Asn Ile Val Ala Gln Arg Tyr Gly Ala Ser Val
        130                 135                 140

Arg Gln Asp Val Leu Gly Asp Leu Met Ser Arg Asn Phe Ile Asp Ala
145                 150                 155                 160

Ile Ile Lys Glu Lys Ile Asn Pro Ala Gly Ala Pro Thr Tyr Val Pro
                165                 170                 175

Gly Glu Tyr Lys Leu Gly Glu Asp Phe Thr Tyr Ser Val Glu Phe Glu
            180                 185                 190

Val Tyr Pro Glu Val Glu Leu Gln Gly Leu Glu Ala Ile Glu Val Glu
        195                 200                 205

Lys Pro Ile Val Glu Val Thr Asp Ala Asp Val Asp Gly Met Leu Asp
        210                 215                 220

Thr Leu Arg Lys Gln Gln Ala Thr Trp Lys Glu Lys Asp Gly Ala Val
225                 230                 235                 240

Glu Ala Glu Asp Arg Val Thr Ile Asp Phe Thr Gly Ser Val Asp Gly
                245                 250                 255

Glu Glu Phe Glu Gly Gly Lys Ala Ser Asp Phe Val Leu Ala Met Gly
            260                 265                 270

Gln Gly Arg Met Ile Pro Gly Phe Glu Asp Gly Ile Lys Gly His Lys
        275                 280                 285

Ala Gly Glu Glu Phe Thr Ile Asp Val Thr Phe Pro Glu Glu Tyr His
```

-continued

```
        290                 295                 300

Ala Glu Asn Leu Lys Gly Lys Ala Ala Lys Phe Ala Ile Asn Leu Lys
305                 310                 315                 320

Lys Val Glu Glu Arg Glu Leu Pro Glu Leu Thr Ala Glu Phe Ile Lys
                325                 330                 335

Arg Phe Gly Val Glu Asp Gly Ser Val Glu Gly Leu Arg Ala Glu Val
                340                 345                 350

Arg Lys Asn Met Glu Arg Glu Leu Lys Ser Ala Ile Arg Asn Arg Val
                355                 360                 365

Lys Ser Gln Ala Ile Glu Gly Leu Val Lys Ala Asn Asp Ile Asp Val
        370                 375                 380

Pro Ala Ala Leu Ile Asp Ser Glu Ile Asp Val Leu Arg Arg Gln Ala
385                 390                 395                 400

Ala Gln Arg Phe Gly Gly Asn Glu Lys Gln Ala Leu Glu Leu Pro Arg
                405                 410                 415

Glu Leu Phe Glu Glu Gln Ala Lys Arg Arg Val Val Val Gly Leu Leu
                420                 425                 430

Leu Gly Glu Val Ile Arg Thr Asn Glu Leu Lys Ala Asp Glu Glu Arg
        435                 440                 445

Val Lys Gly Leu Ile Glu Glu Met Ala Ser Ala Tyr Glu Asp Pro Lys
        450                 455                 460

Glu Val Ile Glu Phe Tyr Ser Lys Asn Lys Glu Leu Met Asp Asn Met
465                 470                 475                 480

Arg Asn Val Ala Leu Glu Glu Gln Ala Val Glu Ala Val Leu Ala Lys
                485                 490                 495

Ala Lys Val Thr Glu Lys Glu Thr Thr Phe Asn Glu Leu Met Asn Gln
                500                 505                 510

Gln Ala
```

HUMAN EPIDERMAL GROWTH FACTOR-TF FUSION PROTEIN AND USE THEREOF

TECHNICAL FIELD

The present invention relates to a novel human epidermal growth factor-TF fusion protein and uses thereof.

BACKGROUND ART

A Human epidermal growth factor (hEGF) has been used to treat general wounds, severe burns, pressure sores, skin ulcers, and venous ulcers on the lower extremities due to its excellent wound healing effect. Recently, it has been known that hEGF regenerates skin cells and promotes the formation of collagen and is also used as a raw material for functional cosmetics.

Although many studies have been conducted for the production of these human epidermal growth factors, various problems occurred during the purification process, in particular, there have been problems that are not suitable for mass production processes due to a decrease in recovery rate that occurs during precipitation and frequent concentration processes. Thereafter, various attempts have been made to express the gene encoding the human epidermal growth factor in *E. coli, Bacillus subtilis*, yeast, etc., but the expression rate in *Bacillus subtilis* and yeast was very low, and when expressed in *E. coli*, the expression rate and yield were low because it is easily degraded by proteolytic enzymes in cells. Thereafter, as a process for obtaining high-purity human epidermal growth factor, a process step such as a high-performance liquid chromatography (HPLC) purification method using a C18 column is required, resulting in a disadvantage that the price was very high.

The ultimate goal in the field of recombinant protein production is to develop a recombinant protein production technology having high specificity and excellent production efficiency. In order to achieve this goal, research on recombinant vectors and host cell systems is being conducted, various expression vectors for expressing a target protein in host cells such as *Bacillus subtilis* and *E. coli* have been developed. However, the expression of the target protein still has a significant degree of defect factors, for example, the recombined protein is converted into an insoluble inclusion body in the host cell or degraded by a proteolytic enzyme, and chemical modification fails during the expression process.

As one of the methods to solve such conventional problems, a factor that promotes the secretion of the recombinant protein is introduced into the vector system to reduce the formation of insoluble inclusion bodies, etc., thereby increasing the expression level of the recombinant protein, that is, the production efficiency. In general, the host cell distinguishes the protein present in the cytoplasm from the protein to be separated out of the cell by the signal peptide present in the precursor protein. In this regard, it has been reported that the precursor protein does not contain a signal peptide so that the protein is not secreted and thus not expressed externally, and the expression pattern of the protein may change depending on the nature of the amino acids constituting the signal peptide. Accordingly, the presence or absence of signal peptides and their properties have an important influence on the production of recombinant proteins.

Meanwhile, in order to obtain an active recombinant protein in *Escherichia coli* in high yield, the most commonly used method is to fuse a fusion partner to the amino terminus of a target protein followed by expression. When expressed by fusion of a fusion partner, there is an advantage in that the target protein can be induced to be water-soluble, and an enzyme is used to remove the fusion partner, thereby solving the problem of methionine at the amino terminus. In fact, several fusion partners that induce high-soluble expression of foreign proteins in *E. coli* have been studied and reported over the past several years.

However, since these fusion partners are relatively large in size compared to the target protein, there are drawbacks in that the yield of the target protein is significantly lowered depending on the size of the fusion part and that they do not work universally for all proteins useful for medical or industrial purposes. Further, in many cases, these fusion partners are formed in a dimer, so the target protein is also produced in the form of a dimer, and even if the expression of the target protein is induced in a water-soluble form, it fails to induce expression in an active form that performs a unique function. In addition, there is a problem in that there is an irrationality in the process that the removal process of the fusion partner must be added in order to be used for a suitable purpose.

So far, domestic recombinant proteins industrially produced by biotechnology have been focused on the development of the production process of recombinant proteins that can be expressed. The development of the expression system, which is a core source technology, is being developed as an additional technology at the level of imitation or improvement compared to foreign countries. In addition, very commercially and medicinally important proteins are secretory proteins and membrane proteins. Since they are difficult-to-express proteins that produce insoluble aggregates when expressed in *E. coli*, development has been delayed.

Therefore, in order to address these issues, it is important to secure the underlying technology by developing an expression system incorporating a signal peptide and a fusion partner to increase the expression efficiency of the real target protein while utilizing the *E. coli* system with various advantages.

DISCLOSURE

Technical Problem

Under this circumstance, the present inventors have made an effort to solve the above problems and construct a recombinant protein expression system capable of producing human epidermal growth factor (hEGF) in a higher yield. As a result, the present inventors have confirmed that the gene construct for the production of the human epidermal growth factor (hEGF)-trigger factor (TF) fusion protein of the present invention is used to improve the function of releasing the hEGF-TF fusion protein of the present invention into the medium, and the produced hEGF-TF fusion protein of the present invention exhibits superior cell growth and wound healing efficacy than commercial hEGF. In addition, it was confirmed that hEGF-TF can be obtained in high yield by applying the optimal conditions for the production of the hEGF-TF fusion protein of the present invention so that the present invention is suitable for mass production processes, thereby completing the present invention.

Accordingly, one object of the present invention is to provide a gene construct for the production of a human epidermal growth factor (hEGF)-trigger factor (TF) fusion protein.

In addition, another object of the present invention is to provide human epidermal growth factor (hEGF)-trigger factor (TF) fusion protein.

In addition, still another object of the present invention is to provide a recombinant expression vector for the production of human epidermal growth factor (hEGF)-trigger factor (TF) fusion protein.

In addition, still another object of the present invention is to provide a transformed recombinant microorganism transformed with the recombinant expression vector.

In addition, yet another object of the present invention is to provide a method for producing human epidermal growth factor (hEGF)-trigger factor (TF) fusion protein.

In addition, yet another object of the present invention is to provide a pharmaceutical composition for treating or preventing skin diseases including human epidermal growth factor (hEGF)-trigger factor (TF) fusion protein as an active ingredient.

In addition, yet another object of the present invention is to provide a food composition for improving skin conditions including human epidermal growth factor (hEGF)-trigger factor (TF) fusion protein as an active ingredient.

In addition, yet another object of the present invention is to provide a cosmetic composition for improving skin conditions including human epidermal growth factor (hEGF)-trigger factor (TF) fusion protein as an active ingredient.

Technical Solution

The terminology used as used herein is only used to describe specific examples and is not intended to limit the present invention. The singular expression includes the plural expression unless the context clearly dictates otherwise. It should be understood that as used herein, terms such as "comprise" or "have" are intended to designate that a feature, step, configuration, or a combination thereof described in the specification exists but do not exclude the possibility of the existence or addition of one or more other features, steps, configurations, or these combinations thereof in advance.

Unless defined otherwise, all terms used herein, including technical and scientific terms, have the same meaning as commonly understood by one of ordinary skill in the art to which this invention belongs. Terms such as those defined in a commonly used dictionary should be interpreted as having a meaning consistent with the meaning in the context of the related art and should not be interpreted in an ideal or excessively formal meaning unless explicitly defined in the present application.

Hereinafter, the present invention will be described in more detail.

According to one aspect of the present invention, the present invention provides a gene construct for the production of human epidermal growth factor (hEGF)-trigger factor (TF) fusion protein, in which the gene construct includes a gene encoding a *Bacillus subtilis*-derived xylanase signal peptide; a gene encoding human epidermal growth factor (hEGF), which is a target protein; and a gene encoding an *Escherichia coli*-derived trigger factor (TF), which is a fusion partner; and in which the gene construct is linked by inserting a TA sequence between the gene encoding the hEGF and the gene encoding the TF.

The gene construct of the present invention may be used by including the nucleotide sequence of any gene encoding *Bacillus subtilis*-derived xylanase signal peptide; any gene encoding human epidermal growth factor; and any gene encoding *E. coli*-derived TF (trigger factor) as long as it may achieve the object of the present invention.

According to a preferred embodiment of the present invention, the gene construct may consist of the nucleotide sequence of SEQ ID NO: 7, but is not limited thereto. In addition, homologs of the nucleotide sequence are included within the scope of the present invention. Specifically, the gene may include a nucleotide sequence having at least 70%, more preferably 80% or more, still more preferably 90% or more, and most preferably 95% or more sequence homology to the nucleotide sequence of SEQ ID NO: 7. The "% of sequence homology" for a polynucleotide is determined by comparing two optimally aligned sequences with a comparison region, in which a portion of the polynucleotide sequence in the comparison region may include additions or deletions (i.e., gaps) compared to a reference sequence (without including additions or deletions) to the optimal alignment of the two sequences.

According to one embodiment of the present invention, the gene encoding the *Bacillus subtilis*-derived xylanase signal peptide may consist of the nucleotide sequence of SEQ ID NO: 1 and may preferably consist of the nucleotide sequence of the *E. coli* codon-optimized SEQ ID NO: 2; the gene encoding the human epidermal growth factor may consist of the nucleotide sequence of SEQ ID NO: 3, preferably composed of the nucleotide sequence of the *E. coli* codon-optimized SEQ ID NO: 4; and the gene encoding the *E. coli*-derived TF (trigger factor) may consist of a nucleotide sequence of SEQ ID NO: 5, but is not limited thereto. In addition, homologs of the nucleotide sequence are included within the scope of the present invention. Specifically, the gene may include a nucleotide sequence having at least 70%, more preferably 80% or more, still more preferably 90% or more, and most preferably 95% or more sequence homology to the nucleotide sequence of SEQ ID NO: 7, respectively.

In addition, the expression as used herein "codon optimization" means a modification of the codon of a polynucleotide encoding a protein, which is used first than others in a specific organism such that the coded protein may be more efficiently expressed. Because most amino acids are described by several codons that are referred to as "synonym" or "synonymous" codon, genetic codes have degeneracy. However, codon usage by a specific organism is not random, and it is rather biased to specific codon triplets. Such codon usage bias may be even higher in relation with a certain gene, a gene with common function or ancestor origin, a protein expressed at high level vs. proteins with low copy number, or a group protein encoding region of a genome of an organism. The nucleotide sequence of SEQ ID NO: 2 or 4 of the present invention is a sequence optimized for the codon of *E. coli* so that the gene encoding the *Bacillus subtilis*-derived xylanase signal peptide or the gene encoding the human epidermal growth factor protein, respectively, may be expressed in *E. coli*.

It was first discovered and demonstrated that in particular, when the TA sequence is inserted and linked between the gene encoding hEGF and the gene encoding the TF in the construct of the present invention, the final product hEGF-TF protein production and secretion amount in the culture medium according to the insertion of the TA sequence was significantly increased.

In addition, according to another aspect of the present invention, the present invention provides a human epidermal growth factor (hEGF)-trigger factor (TF) fusion protein.

The fusion protein of the present invention means an hEGF-TF fusion protein in which *Bacillus subtilis*-derived xylanase signal peptide and *E. coli*-derived TF are artificially recombined (fused) to bind to the N-terminus and C-terminus of human epidermal growth factor, respectively, and as used herein, it is used interchangeably with "hEGF-TF protein," "hEGF-TF," "fusion protein," or "recombinant protein."

In the present invention, the hEGF-TF fusion protein of the present invention is a novel protein consisting of the amino acid sequence of SEQ ID NO: 11 and exhibits increased cell growth and wound healing effects.

The scope of the hEGF-TF fusion protein with increased cell growth and wound healing effects according to the present invention includes a protein having the amino acid sequence of SEQ ID NO: 11 and functional equivalents of the protein. The term "Functional equivalent" means one having a sequence homology of at least 70% or more, preferably 80% or more, more preferably 90% or more, even more preferably 95% or more of the amino acid sequence of SEQ ID NO: 11 as a result of addition, substitution or deletion of amino acids, and it refers to a protein that exhibits substantially the same activity as the protein of SEQ ID NO: 11. The term "substantially homogeneous activity" refers to the activity of cell proliferation, growth, and survival enhancement and wound healing.

According to one embodiment of the present invention, the *Bacillus subtilis*-derived xylanase signal peptide consists of the amino acid sequence of SEQ ID NO: 8; the human epidermal growth factor consists of the amino acid sequence of SEQ ID NO: 9; and the *E. coli*-derived trigger factor (TF) consists of the amino acid sequence of SEQ ID NO: 10.

In the present invention, in the fusion protein, the *Bacillus subtilis*-derived xylanase signal peptide and *E. coli*-derived trigger factor (TF), respectively, may be directly linked to the N-terminus and C-terminus of the EGF and may be linked through a linker. The linker is not specifically limited, as long as it shows the effect of enhancing the enzymatic activity of the fusion protein. Preferably, it may be linked by amino acids such as glycine, alanine, leucine, iso-leucine, proline, serine, threonine, asparagine, aspartic acid, cysteine, glutamine, glutamic acid, lysine, and argininic acid. More preferably, it may be linked by using some among valine, leucine, aspartic acid, glycine, alanine, proline and the like. Most preferably, it may be linked by using 1 to 5 amino acids of glycine, valine, leucine, aspartic acid and the like considering the ease of genetic manipulation.

The fusion protein may include a polypeptide having one or more amino acid residues having the sequence different from the wild-type amino acid sequence of each domain included therein. Amino acid exchanges in proteins and polypeptides that do not entirely alter the activity of the molecule are known in the art. The most commonly occurring exchange is the exchange between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In addition, it may include a protein in which structural stability to heat, pH, etc. of the protein is increased or protein activity is increased due to mutation or modification in the amino acid sequence.

The fusion protein or the polypeptide constituting the fusion protein is prepared by a chemical peptide synthesis method known in the art, or by amplifying the gene encoding the fusion protein by using polymerase chain reaction (PCR) or synthesizing by using a known method to clone into an expression vector and express the same.

In addition, according to still another aspect of the present invention, the present invention provides a recombinant expression vector for the production of human epidermal growth factor (hEGF)-trigger factor (TF) fusion protein including the above-described gene construct and a host cell which is a transformed recombinant microorganism transformed with the recombinant expression vector.

The term "recombinant" refers to a cell in which the cell replicates or expresses a heterologous nucleic acid, or expresses a peptide, heterologous peptide or protein encoded by the heterologous nucleic acid. A recombinant cell may express a gene or a gene fragment in the form of a sense or antisense, which are not found in natural state of cell. In addition, a recombinant cell may express a gene that is found in natural state of cell, provided that said gene is modified and re-introduced into the cell by an artificial means.

In the present invention, the hEGF-TF encoding gene with increased cell growth and wound healing effects may be inserted into a recombinant expression vector. The term "recombinant expression vector" means a bacterial plasmid, phage, yeast plasmid, plant cell virus, mammalian cell virus, or other vector. In general, any plasmid and vector may be used as long as it is capable of replication and stabilization in the host. An important characteristic of the expression vector is that it has an origin of replication, a promoter, a marker gene and a translation control element.

An expression vector including a gene sequence encoding an hEGF-TF fusion protein having an increased cell growth and wound healing effect and an appropriate transcription/translation control signal may be constructed by a method well known to those skilled in the art. The method includes in vitro recombinant DNA technology, DNA synthesis technology, in vivo recombination technology, and the like. To induce mRNA synthesis, the DNA sequence may be effectively linked to a suitable promoter in an expression vector. Further, the expression vector may include, as a translation initiation region, a ribosome binding site and a transcription terminator.

As a host cell capable of stably continuously cloning and expressing the vector of the present invention in a prokaryotic cell, any host cell known in the art may be used, for example, *E. coli* BL21, *E. coli* Rosetta, *E. coli* JM109, *E. coli* RR1, *E. coli* LE392, *E. coli* B, *E. coli* X 1776, *E. coli* W3110, *Bacillus* genus strains such as *Bacillus subtilis* and *Bacillus thuringiensis*, and Enterobacteriaceae class strain such as *Salmonella typhimurium, Serratia marcescens* and various *Pseudomonas* species and the like.

In addition, when the vector of the present invention is transformed into a eukaryotic cell, yeast (*Saccharomyces cerevisiae*), insect cell, human cell (e.g., CHO cell line (Chinese hamster ovary), W138, BHK, COS-7, 293, HepG2, 3T3, RIN and MDCK cell lines) and plant cells may be used as a host cell.

The host cell transformed with the recombinant vector according to an embodiment of the present invention may be preferably *E. coli*, more preferably *E. coli* BL21 (DE3), but is not limited thereto.

The method of transferring the vector of the present invention into a host cell may be carried out by the CaCl$_2$) method, Hanahan method, electroporation method, etc., when the host cell is a prokaryotic cell. In addition, when the host cell is a eukaryotic cell, the vector may be injected into the host cell by microinjection, calcium phosphate precipitation, electroporation, liposome-mediated transfection, DEAE-dextran treatment, gene bombardment, and the like.

In addition, a polynucleotide encoding a tag for separation and purification may be operatively linked to the fusion partner of the vector of the present invention or the gene of the target protein to facilitate the separation and purification of the recombinant protein.

The target gene may be cloned through a restriction enzyme site, and when a polynucleotide encoding a protein cleavage enzyme recognition site is used, it is linked in frame with the polynucleotide. Thus, the target protein is secreted and then cut with a proteolytic enzyme, allowing the production of the foreign protein having the original form.

As used herein, the term "operably linked" refers to a state in which a nucleic acid expression control sequence and a nucleic acid sequence encoding a target protein or RNA are functionally linked so as to perform a general function. For example, a promoter and a nucleic acid sequence encoding a protein or RNA may be operably linked to affect the expression of the coding sequence. The operative linkage with the expression vector may be prepared by using a genetic recombination technique well known in the art, and site-specific DNA cleavage and ligation may be performed by using enzymes generally known in the art.

In addition, according to still another aspect of the present invention, the present invention provides a method for producing human epidermal growth factor (hEGF)-trigger factor (TF) fusion protein, the method including steps of:

(a) preparing a recombinant expression vector including the construct fused with a gene encoding a *Bacillus subtilis*-derived xylanase signal peptide; a gene encoding human epidermal growth factor (hEGF), which is a target protein; and a gene encoding an *Escherichia coli*-derived trigger factor (TF), which is a fusion partner, in which the gene construct is linked by inserting a TA sequence between the gene encoding the hEGF and the gene encoding the TF;

(b) preparing a transformant by introducing the recombinant expression vector of step (a) into a microorganism; and (c) culturing the transformant of step (b) to induce the expression of human epidermal growth factor (hEGF)-trigger factor (TF) fusion protein, thereby obtaining the same.

Preferably, step (c) further includes step of culturing the transformant at a high concentration and replacing the medium before inducing the expression of the human epidermal growth factor (hEGF)-trigger factor (TF) fusion protein, thereby significantly increasing the production yield of the hEGF-TF fusion protein.

In other words, the present invention provides conditions and methods for inducing protein expression for increasing hEGF-TF fusion protein production.

More specifically, provided is a method of preparing a recombinant protein including steps of linking a signal peptide and a fusion partner to a gene of a target protein, preparing an expression vector into which a TA sequence is introduced, preparing a transformant by introducing the expression vector into a host cell and inducing expression of a recombinant protein by culturing the transformant and obtaining the same. The method increases the excretion of the recombinant protein into the culture medium by introducing a *Bacillus subtilis*-derived xylanase signal peptide into the culture medium of the recombinant protein and improves the solubility of the recombinant protein by using *E. coli*-derived trigger factor (TF) gene as a fusion partner to express the same.

As used herein, the term "culture" refers to culturing of a microorganism under artificially controlled environmental conditions. In the present invention, the method for culturing the transformant may be conducted using a method widely known in the art. Specifically, the culture is not particularly limited as long as it may be produced by expressing the fusion protein of the present invention, but it may be continuously cultured in a batch, fed batch, or repeated fed batch process.

The medium used for culture should comply with the requirements of a specific strain in an appropriate manner while controlling temperature, pH, etc. under aerobic conditions in a typical medium containing an appropriate carbon source, nitrogen source, amino acids, vitamins, and the like. As a carbon source that may be used, a mixed sugar of glucose and xylose is used as the main carbon source. In addition to these carbon sources, it includes sugars and carbohydrates such as sucrose, lactose, fructose, maltose, starch, cellulose, oils and fats such as soybean oil, sunflower oil, castor oil, and coconut oil, fatty acids such as palmitic acid, stearic acid and linoleic acid, alcohols such as glycerol and ethanol, and organic acids such as acetic acid. These substances may be used separately or in combination. Nitrogen source that may be used includes inorganic nitrogen sources such as ammonia, ammonium sulfate, ammonium chloride, ammonium acetate, ammonium phosphate, ammonium carbonate, and ammonium nitrate; amino acids such as glutamic acid, methionine, and glutamine, and organic nitrogen sources such as peptone, NZ-amine, meat extract, yeast extract, malt extract, corn steep liquor, casein hydrolyzate, fish or its degradation products, defatted soybean cake or its degradation products, etc. These nitrogen sources may be used alone or in combination. The medium may include monopotassium phosphate, dipotassium phosphate and the corresponding sodium-containing salt as a phosphorus source. The phosphorus source that may be used includes potassium dihydrogen phosphate or dipotassium hydrogen phosphate or the corresponding sodium-containing salt. In addition, sodium chloride, calcium chloride, iron chloride, magnesium sulfate, iron sulfate, manganese sulfate, calcium carbonate, etc. may be used as the inorganic compound. Finally, in addition to the above substances, essential growth substances such as amino acids and vitamins may be used.

In addition, precursors suitable for the culture medium may be used. The above-mentioned raw materials may be added in a batch, fed-batch or continuous manner by an appropriate method to the culture during the culturing process, but is not particularly limited thereto. Basic compounds such as sodium hydroxide, potassium hydroxide, ammonia or acid compounds such as phosphoric acid or sulfuric acid may be used in an appropriate manner to adjust the pH of the culture.

In addition, the step of recovering the fusion protein from the culture may be performed by a method known in the art. Specifically, the recovery method is not particularly limited as long as the produced fusion protein of the present invention may be recovered, but preferably a method such as centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion) and the like may be used.

In addition, according to still another aspect of the present invention, the present invention provides a pharmaceutical composition for treating or preventing skin diseases including human epidermal growth factor (hEGF)-trigger factor (TF) fusion protein as an active ingredient.

As used herein, the term "prevention" refers to any action that inhibits or delays skin diseases by administration of the pharmaceutical composition. In addition, the term "treatment" refers to any action that improves or beneficially changes the symptoms of skin diseases by administration of the pharmaceutical composition.

In one example of the present invention, the hEGF-TF fusion protein of the present invention exhibits superior cell growth and wound healing effects than commercially available hEGF.

Through previous studies, the epidermal growth factor is known to mainly stimulate the regeneration and differentiation of intestinal mucosa, corneal epithelial tissue, and lung epidermal tissue, thereby promoting epidermal proliferation, promoting angiogenesis, enhancing wound healing, and inhibiting gastric acid secretion. Since it was confirmed that the fusion protein provided in the present invention may improve the effect of EGF, the hEGF-TF fusion protein of the present invention may be variously applied to the prevention or treatment of skin wounds and skin aging (decreased elasticity), as well as diseases in which EGF protein has been used in the past, that is, atopic dermatitis, contact dermatitis, corneal disease and gastric ulcer.

As used herein, the term "skin disease" includes, but is not limited to, wounds, cuts, psoriasis, atopic dermatitis, contact dermatitis, foot ulcer, pressure ulcer, oral mucositis, or burns.

The pharmaceutical composition of the present invention may be prepared in unit dosage form or through incorporation into a multi-dose container by formulating using a pharmaceutically acceptable carrier and/or excipient according to a method that may be easily carried out by a person of ordinary skill in the art to which the present invention pertains. In this case, the formulation may be in the form of a solution, suspension, syrup, or emulsion in oil or an aqueous medium, or may be in the form of an extract, powder remedy, powder, granule, tablet or capsule, and may additionally include a dispersant or stabilizer.

The pharmaceutical composition prepared as described above may be administered in a parenteral manner, that is, subcutaneously, intramuscularly, or topically, depending on the purpose. The dose may be administered in a daily dose of 0.01 ng to 10,000 mg/kg divided into one to several times. The dosage level for a specific patient may vary depending on the patient's weight, age, sex, health status, administration time, administration method, disease severity, and the like.

In addition, the present invention may provide a pharmaceutical composition for external preparation for skin including the fusion protein.

As used herein, the term "external preparation for skin" refers to a solid, semi-solid, or liquid external preparation that may be easily applied to the skin by mixing drugs with various bases such as oils and fats, petrolatum, lanolin, and glycerol. Formulations for external use are not particularly limited, but preferably include powder, gel, ointment, cream, liquid or aerosol formulations.

For the purpose of the present invention, the external preparation for skin may be interpreted as a preparation including the fusion protein of the present invention and a base that is an appropriate carrier for external preparation for skin, but is not particularly limited thereto.

In addition, the composition of the present invention includes the above-described fusion protein of the present invention as an active ingredient, but redundant descriptions thereof will be omitted in order to avoid excessive complexity of the present specification.

In addition, according to still another aspect of the present invention, the present invention provides a food composition or functional food composition for improving skin conditions including the human epidermal growth factor (hEGF)-trigger factor (TF) fusion protein as an active ingredient.

When the composition including the hEGF-TF fusion protein of the present invention is prepared as a functional food composition or a food composition, it contains not only the hEGF-TF fusion protein as an active ingredient, but also a component commonly added during the functional food or production of food, for example, proteins, carbohydrates, fats, nutrients, seasonings, and flavoring agents. Examples of the carbohydrates include monosaccharides such as glucose, fructose, and the like; disaccharides such as maltose, sucrose, oligosaccharides, and the like; and polysaccharides such as conventional sugars including dextrin, cyclodextrin, and the like, and sugar alcohols such as xylitol, sorbitol, and erythritol. As the flavoring agent, natural flavoring agents (thaumatin, *stevia* extract (e.g., rebaudioside A, glycyrrhizin, etc.)) and synthetic flavoring agents (saccharin, aspartame, etc.) may be used.

When the functional food or food composition of the present invention is prepared as a drink, citric acid, liquid fructose, sugar, glucose, acetic acid, malic acid, fruit juice, eucommia ulmoides extract, jujube extract or licorice extract, etc. may be additionally included in addition to the active ingredient of the present invention.

In addition, the composition of the present invention includes the above-described fusion protein of the present invention as an active ingredient, but redundant descriptions thereof will be omitted in order to avoid excessive complexity of the present specification.

In addition, according to still another aspect of the present invention, the present invention provides a cosmetic composition for improving skin conditions including the above-described human epidermal growth factor (hEGF)-trigger factor (TF) fusion protein as an active ingredient.

As used herein, the term "improving skin condition" comprehensively refers to a process for treating, relieving, or alleviating skin damage caused by intrinsic or extrinsic factors of the skin, or its effects, and more specifically, skin anti-aging, skin elasticity improvement, skin regeneration, wound or cuts recovery, corneal regeneration, skin irritation relief, etc., which may be induced by applying the fusion protein of the present invention on the skin.

In the cosmetic composition according to an embodiment of the present invention, the content of the fusion protein of the present invention is preferably included in an amount of 0.000001% by weight to 10% by weight based on the total weight of the cosmetic composition.

When the content of the protein is less than 0.000001% by weight, the effect of improving wrinkles and maintaining skin elasticity is insignificant, and when it is 10% by weight or more, the degree of increase in the effect of increasing the content is insignificant, and there may be problems in safety and stability of the formulation.

The cosmetic composition of the present invention includes ingredients commonly used in cosmetic compositions, in addition to the active ingredients, for example, conventional adjuvants such as fatty substance, organic solvent, solubilizing agent, thickener, gelling agent, softener, antioxidant, suspending agent, stabilizer, foaming agent, fragrance, surfactant, water, ionic or non-ionic emulsifying agent, filler, metallic ion sequester, chelating agent, preservative, vitamins, blocking agent, wetting agent, essential oil, dye, pigment, hydrophilic or lipophilic activator, and lipid vesicle and carriers.

The composition of the present invention may be prepared in any formulation conventionally prepared in the art, but for example may be formulated as solution, suspension, emulsion, paste, gel, cream, lotion, powder, oil, powder foundation, emulsion foundation, wax foundation, and spray, but is not limited thereto. More specifically, it may be prepared in cosmetic formulations of skin, skin softener, skin toner, astringent, lotion, milk lotion, moisture lotion, nourishing lotion, massage cream, nourishing cream, eye cream, moisture cream, hand cream, essence, nourishing essence, pack, cleansing foam, cleansing water, cleansing lotion, cleansing cream, body lotion, body cleanser, soap and powder.

When the cosmetic composition of the present invention is formulated in a paste, cream or gel, the carrier component may include animal oil, vegetable oil, wax, paraffin, starch, tragacanth, cellulose derivative, polyethylene glycol, silicone, bentonite, silica, talc, zinc oxide, or the like.

When the cosmetic composition of the present invention is formulated in a powder or a spray, the carrier component may include lactose, talc, silica, aluminum hydroxide, calcium silicate or polyamide powder. In particular, in the case of a spray, additional propellants such as chlorofluoro hydrocarbons, propane/butane or dimethyl ether.

When the cosmetic composition of the present invention is formulated in a solution or emulsion, the carrier component may include a solvent, solubilizer or emulsifier, for example, water, ethanol, isopropanol, ethyl carbonate, ethyl acetate, benzyl alcohol, benzyl benzoate, propylene glycol, 1,3-butylglycol oil, glycerol fatty ester, polyethylene glycol or sorbitan fatty acid esters.

When the cosmetic composition of the present invention is formulated in a suspension, the carrier component may include a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, or the like.

In addition, the present invention may provide a functional cosmetic including the cosmetic composition for improving skin condition.

As used herein, the term "cosmedical or cosmeceutical" of the present invention refers to a product with professional functionalities that emphasizes physiologically active efficacy and effect, unlike general cosmetics, in which the professional therapeutic function of pharmaceuticals is introduced into cosmetics. It refers to cosmetics prescribed by the Ordinance of the Ministry of Health and Welfare among products that help to improve skin wrinkles and products that help to enhance skin elasticity.

The cosmedical may be prepared by adding an appropriate carrier used in the preparation of general skin cosmetics to the cosmetic composition of the present invention. In this case, the carrier used is not particularly limited thereto, but preferably oil, water, surfactant, humectant, lower alcohol, thickener, chelating agent, colorant, preservative, fragrance, etc. may be used alone or in an appropriate combination.

The cosmedical of the present invention exhibits skin condition improvement effects such as skin cell growth promotion and wound healing effects, and the formulation thereof is not particularly limited, but for example, it may be prepared in the form of solution, emulsion, suspensions, paste, cream, lotion, gel, powder, spray, surfactant-containing cleansing, oil, soap, liquid detergent, bath agent, foundation, makeup base, essence, lotion, foam, pack, soft water, sunscreen cream, sun oil, and the like. Preferably, it may be prepared in the form of an external skin ointment, softening lotion, nourishing lotion, nourishing cream, massage cream, essence, pack, emulsion or oil gel. In this case, the carrier used may be selectively used according to the cosmetic formulation.

For example, when cosmetics are prepared in the form of ointment, paste, cream or gel, wax, paraffin, starch, tragacanth, cellulose derivatives, polyethylene glycol, silicone, bentonite, silica, talc, zinc oxide, etc. may be used alone or in combination as carrier components; when cosmetics are prepared in the form of powder or spray cosmetics, lactose, talc, silica, aluminum hydroxide, calcium silicate, polyamide powder, chlorofluorohydrocarbon, propane/butane, dimethyl ether, etc. may be used alone or in combination as carrier components; when cosmetics are prepared in the form of solution or emulsion, water, ethanol, isopropanol, ethyl carbonate, ethyl acetate, benzyl alcohol, benzyl benzoate, propylene glycol, 1,3-butyl glycol oil, cottonseed oil, peanuts oil, corn germ oil, olive oil, castor oil, sesame oil, glycerol fatty ester, polyethylene glycol or fatty acid ester of sorbitan, etc. may be used alone or in combination as carrier components; when cosmetics are prepared in the form of a suspension, water, ethanol or propylene glycol, ethoxylated isostearyl alcohol, polyoxyethylene sorbitol ester, polyoxyethylene sorbitan ester, microcrystalline cellulose, aluminum metahydroxide, bentonite, agar, tragacanth, etc, may be used alone or in combination as carrier components; and when cosmetics are prepared in the form of cosmetic soap, alkali metal salt, fatty acid hemiester salt, fatty acid protein hydrolysate, isethionate, lanolin derivative, aliphatic alcohol, vegetable oil, glycerol, sugar, etc. may be used alone or in combination as carrier components.

The composition of the present invention includes the above-described fusion protein of the present invention as an active ingredient, but redundant descriptions thereof will be omitted in order to avoid excessive complexity of the present specification.

In addition, according to still another aspect of the present invention, the present invention provides a method for treating or preventing a skin disease including administering the human epidermal growth factor (hEGF)-trigger factor (TF) fusion protein to a subject.

It may be administered in the form of a pharmaceutical composition including the hEGF-TF fusion protein, and the composition administration method is the same as that of the pharmaceutical composition.

In addition, the composition of the present invention includes the above-described fusion protein of the present invention as an active ingredient, but redundant descriptions thereof will be omitted in order to avoid the excessive complexity of the present specification.

Advantageous Effects

In the human epidermal growth factor (hEGF)-trigger factor (TF) fusion protein of the present invention, a signal peptide of *Bacillus subtilis*-derived xylanase; human epidermal growth factor (hEGF); and *E. coli*-derived trigger factor (TF) are linked to improve the water solubility and expression rate of the target protein and to significantly enhance useful effects such as skin cell growth increase and wound healing effect so that it will be widely used in various industries as active ingredients of cosmedical compositions and pharmaceutical compositions for improving skin condition or preventing aging for wrinkle improvement and skin regeneration promotion as well as therapeutic agents for skin diseases such as intractable chronic skin ulcers and gastric ulcers.

hEGF-TF (A): a construct composed of a signal peptide of *Bacillus subtilis*-derived xylanase signal peptide; human epidermal growth factor (hEGF) and *E. coli*-derived trigger factor (TF), hEGF-TF (B): a construct composed of a signal peptide of *Bacillus subtilis*-derived xylanase signal peptide; human epidermal growth factor (hEGF) and *E. coli*-derived trigger factor (TF) linked by TA.

Figure 2:
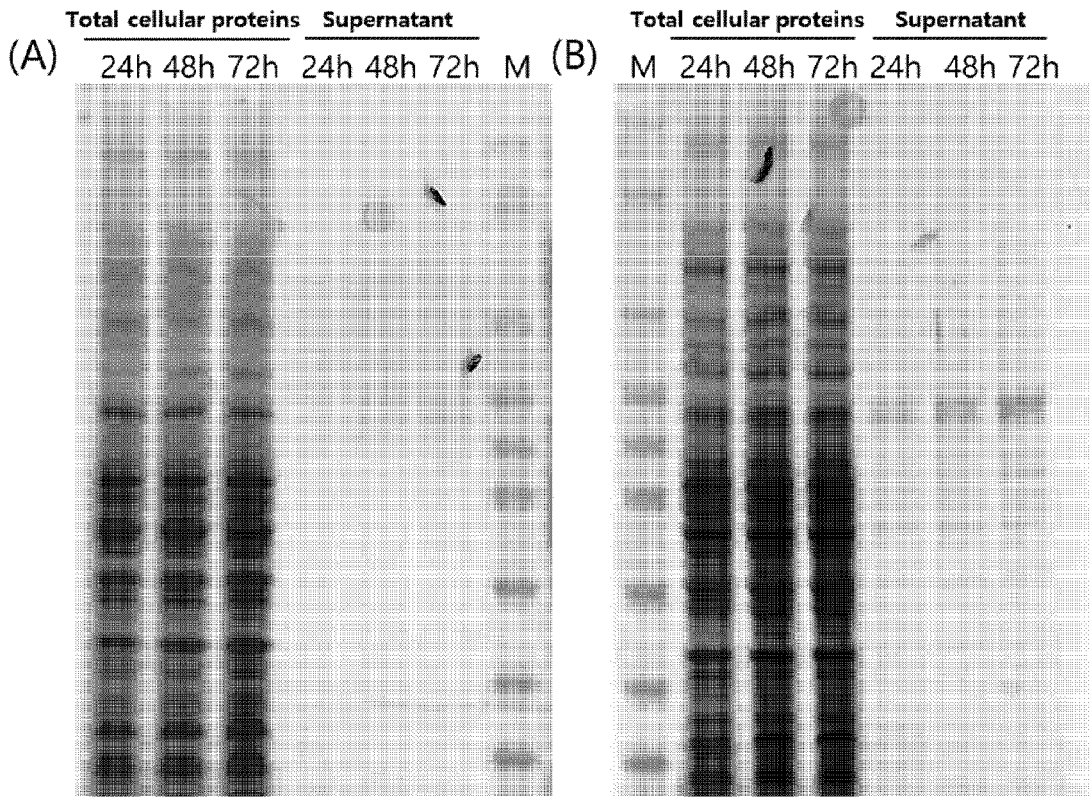

FIG. 2 is the result of confirming the amount of intracellular protein and protein secreted into the culture medium over time by SDS-PAGE for an hEGF-TF (A) construct-inserted into *E. coli* BL21 (DE3) under various conditions to establish optimal conditions for increasing the production (secreted amount) of the hEGF-TF fusion protein of the present invention; FIG. 2A shows the result of culturing to 0.8 at OD600 nm and inducing expression after the addition of IPTG; and FIG. 2B shows the result of culturing to 2.5 at OD600 nm, replacing the medium and then inducing expression after the addition of IPTG.

Figure 3:
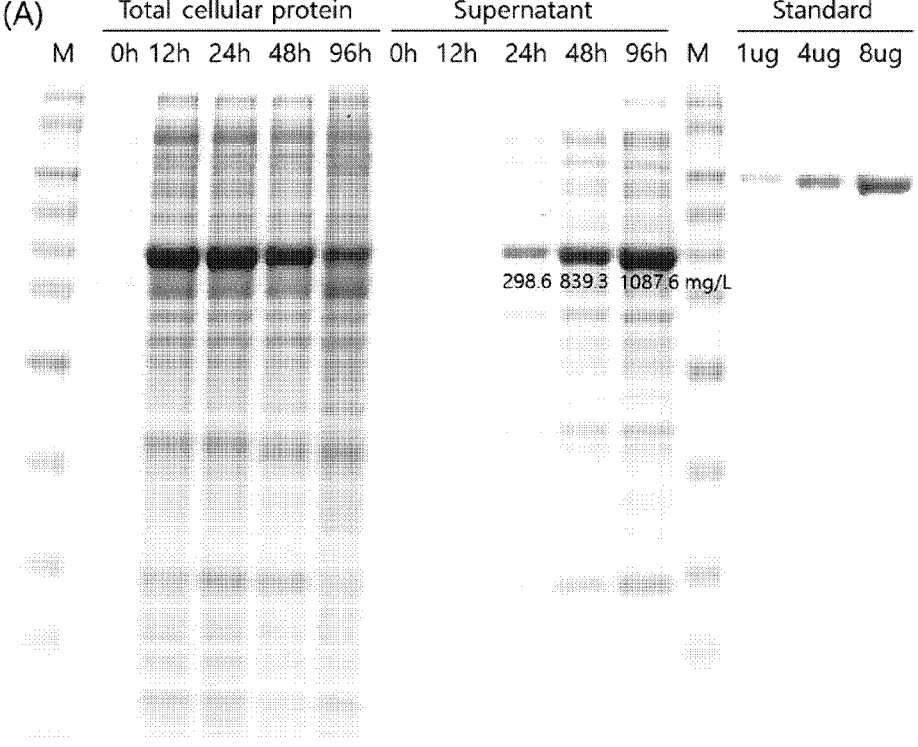
Figure 3:
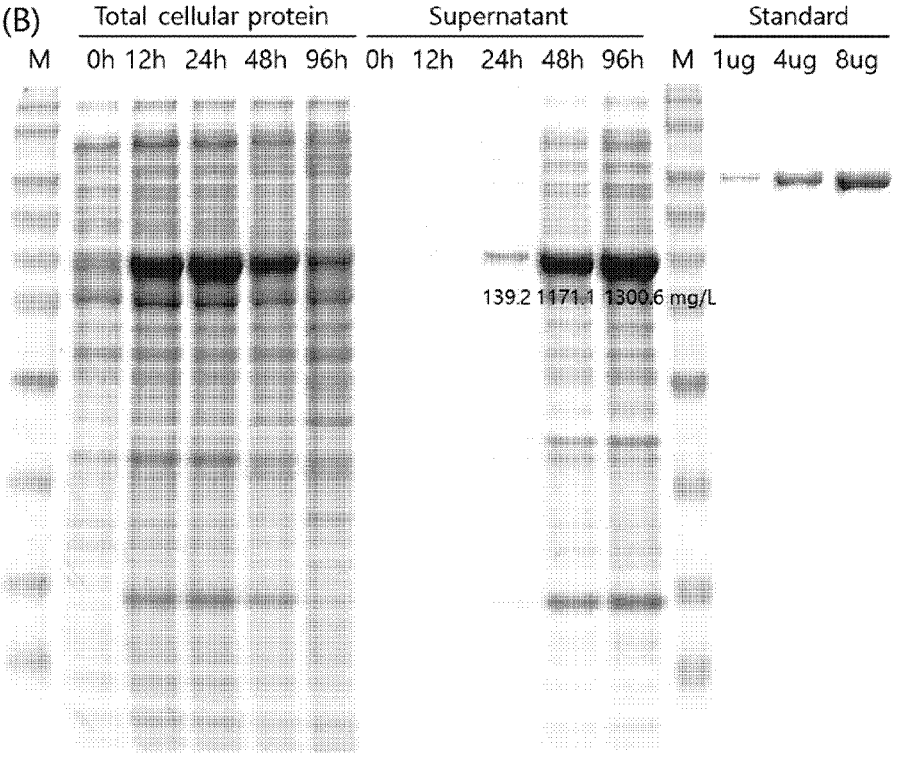

FIG. 3 is the result of confirming the amount of intracellular protein and protein secreted into the culture medium over time by SDS-PAGE for an hEGF-TF (B) construct-inserted into *E. coli* BL21 (DE3) under various conditions to establish optimal conditions for increasing the production (secreted amount) of the hEGF-TF fusion protein of the present invention; FIG. 3A shows the result of culturing to 0.8 at OD600 nm and inducing expression after the addition of IPTG; and FIG. 3B shows the result of culturing to 2.5 at OD600 nm, replacing the medium and then inducing expression after the addition of IPTG.

Figure 4:
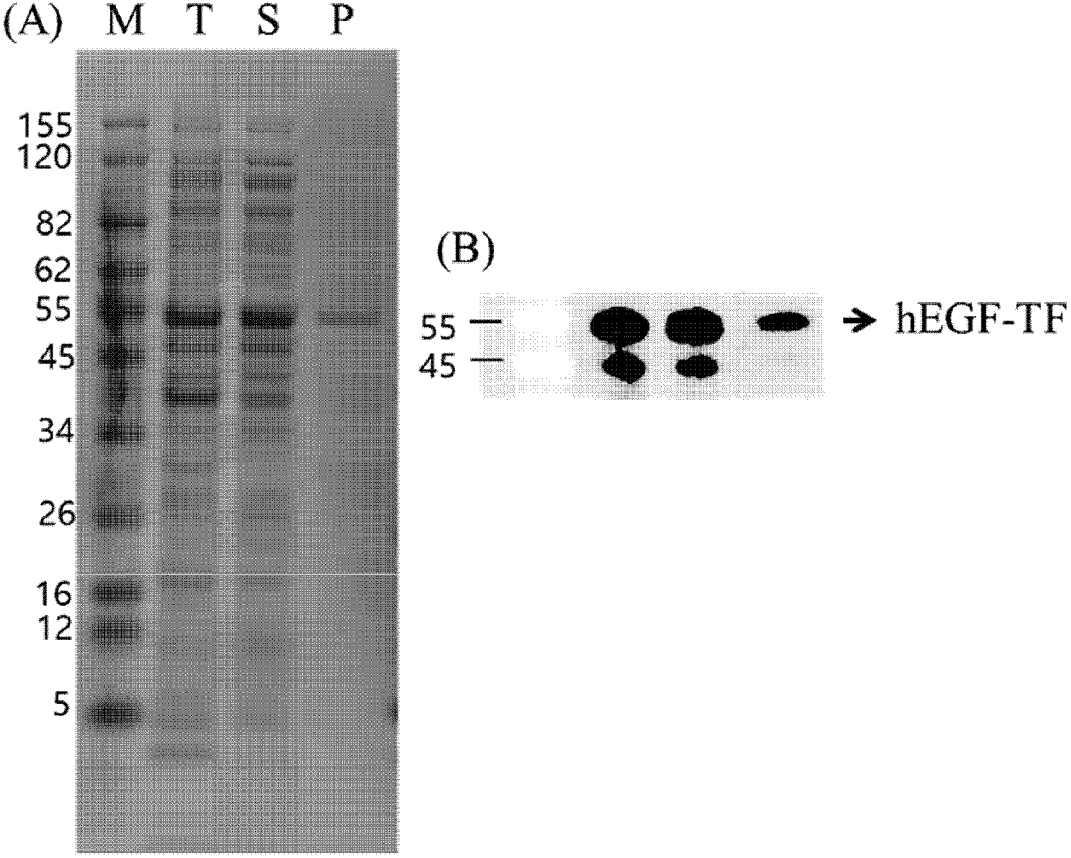

FIG. 4 is a result of confirming the protein purified by osmotic pressure by SDS-PAGE (A) and Western blot (B).

Figure 5:
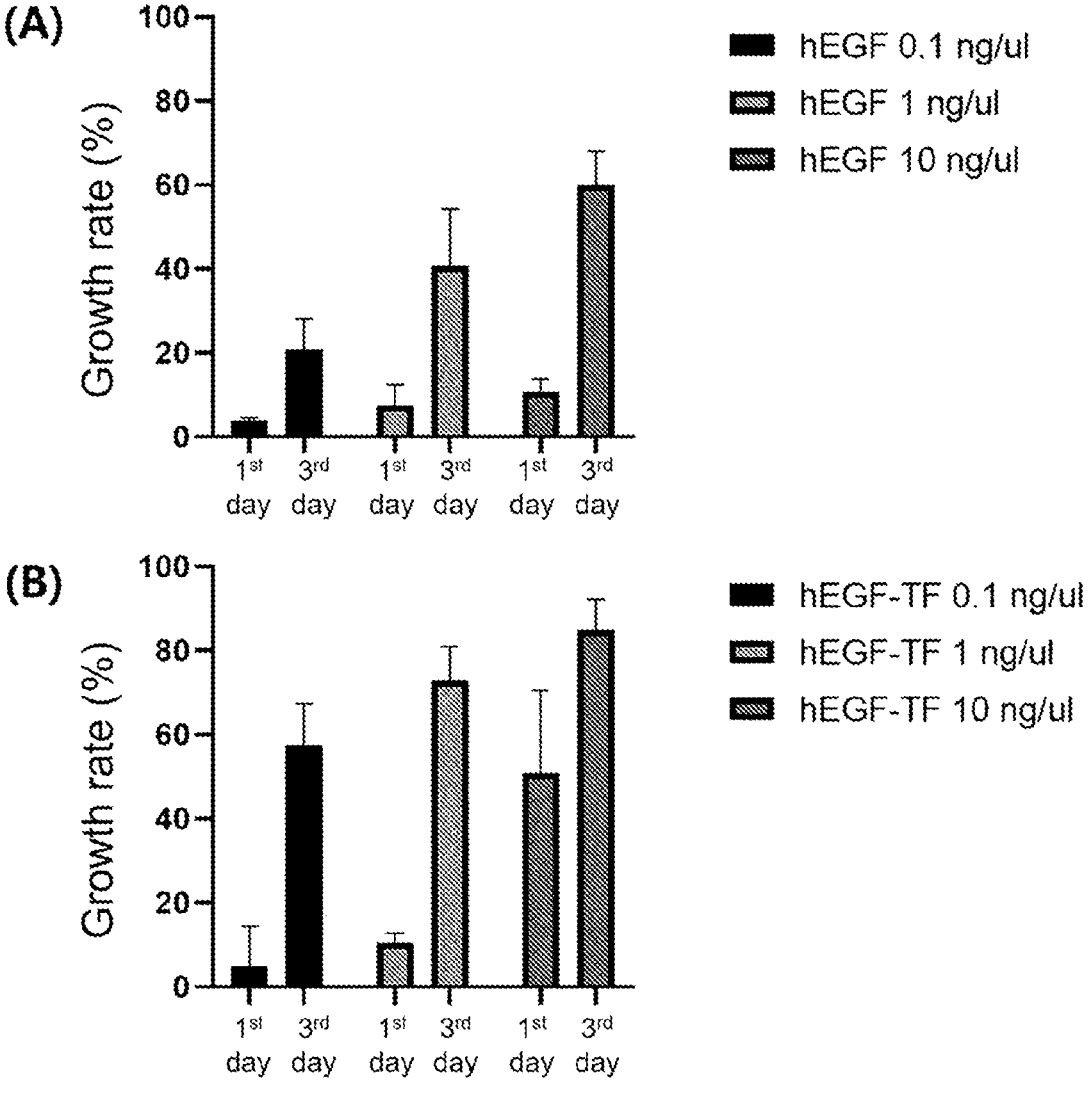

FIG. 5 is a result of showing the cell regeneration effect of commercially available hEGF (A) and hEGF-TF (B) on fibroblasts.

Figure 6:
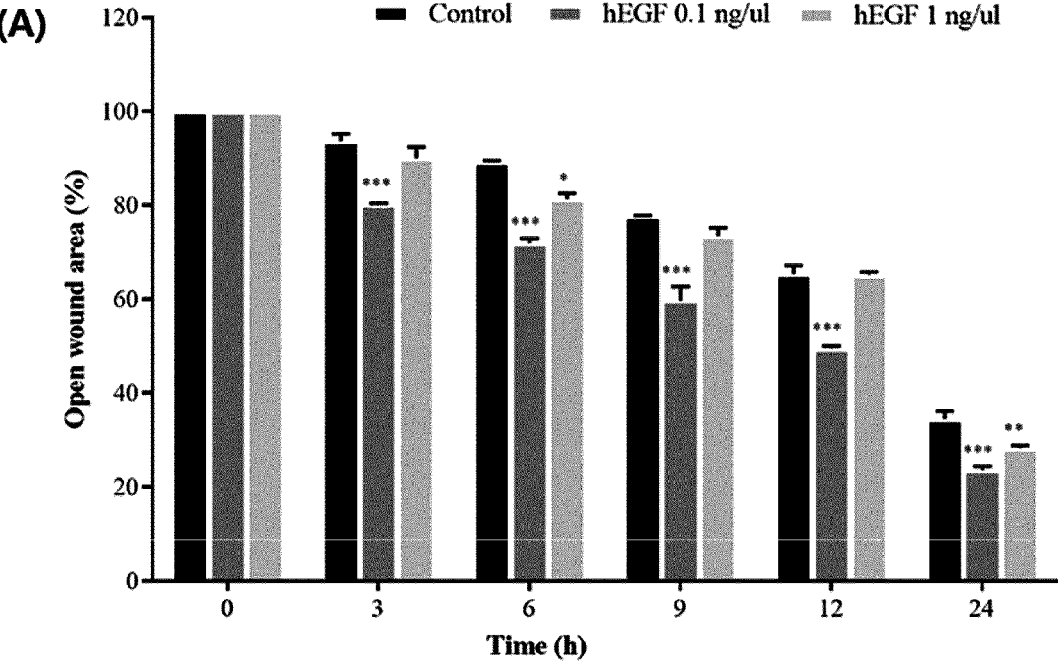
Figure 6:
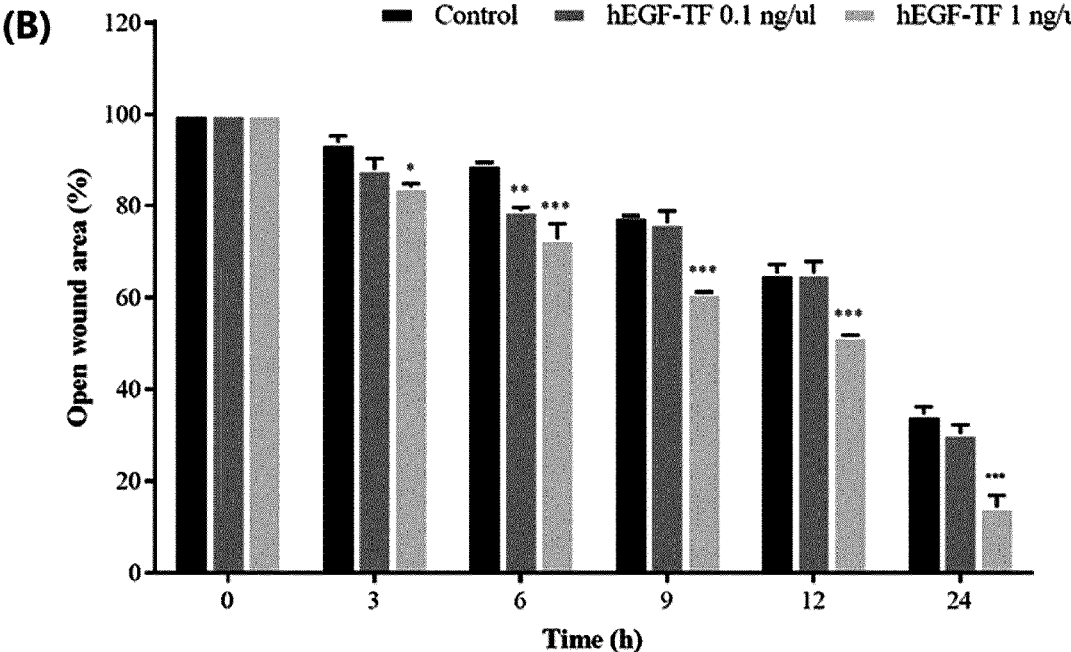

FIG. 6 is a result of showing the wound healing effect of commercially available hEGF (A) and hEGF-TF (B) on fibroblasts.

MODES OF THE INVENTION

Hereinafter, it will be obvious to those of ordinary skill in the art to which the present invention pertains that the examples are only for explaining the present invention in more detail, and the scope of the present invention is not limited by these examples according to the gist of the present invention.

Example 1. Manufacture of the Recombinant Expression Vector and Transformed Recombinant Microorganism for the Production of Human Epidermal Growth Factor (hEGF)-Trigger Factor (TF) Fusion Protein The present inventors have prepared a construct, a recombinant expression vector, and a transformed recombinant microorganism for producing the novel hEGF-TF fusion protein of the present invention as follows.

Figure 1:
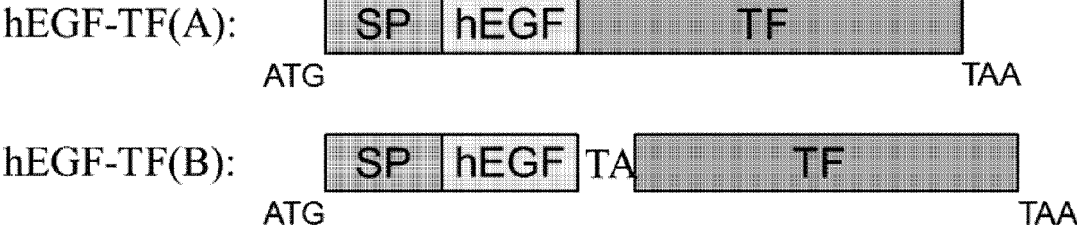
FIG. 1 shows a gene construct used in this example.

First, as shown in FIG. 1, a gene encoding human epidermal growth factor (hEGF), which is a target protein and a gene encoding a trigger factor (TF) derived from *E. coli*, which is a fusion partner protein for producing the hEGF protein in *E. coli* in a water-soluble state, were linked; at this time, a TA sequence was additionally inserted between the gene encoding hEGF and the gene encoding TF; and the construct hEGF-TF (B) (SEQ ID NO: 7), to which the gene encoding a *Bacillus subtilis*-derived xylanase signal peptide was ligated, was designed such that the *Bacillus subtilis*-derived xylanase signal peptide as a signal peptide for secreting the hEGF-TF fusion protein into the culture medium was linked to the N-terminus of the hEGF-TF fusion protein.

In addition, codon-optimized sequences were used for the gene encoding the *Bacillus subtilis*-derived xylanase signal peptide and the gene encoding hEGF and are represented by SEQ ID NO: 2 and SEQ ID NO: 4, respectively.

Here, as a control to check the effect difference depending on whether the TA sequence is inserted or not, the construct hEGF-TF (A) (SEQ ID NO: 6) in which the gene encoding hEGF and the gene encoding TF were directly linked without inserting a TA sequence was used.

The hEGF-TF construct sequence and the hEGF-TF fusion protein sequence used in this example are listed in Table 1.

More specifically, the codon-optimized gene sequence encoding *Bacillus subtilis*-derived xylanase signal peptide is represented by SEQ ID NO: 2; the codon-optimized gene sequence encoding EGF is represented by SEQ ID NO: 4; the gene sequence encoding TF is represented by SEQ ID NO: 5; the construct including the signal peptide-EGF-TF gene (hEGF-TF (A)) is represented by SEQ ID NO: 6; and a construct (hEGF-TF (B)) linked by a TA sequence between the signal peptide-EGF and the TF genes is represented by SEQ ID NO: 7.

Further, in SEQ ID NOs: 6 and 7, the gene sequence encoding *Bacillus subtilis*-derived xylanase signal peptide is underlined; the gene sequence encoding EGF is shown in bold; and the gene sequences encoding TFs are shown in italics.

In addition, the amino acid sequence of the *Bacillus subtilis*-derived xylanase signal peptide is represented by SEQ ID NO: 8; the amino acid sequence of EGF is represented by SEQ ID NO: 9; the amino acid sequence of TF is represented by SEQ ID NO: 10; and the amino acid sequence of the signal peptide-EGF-TF is represented by SEQ ID NO: 11.

Further, in SEQ ID NO: 11, the sequence of *Bacillus subtilis*-derived xylanase signal peptide is underlined; the sequence of EGF is shown in bold; and the sequence of TF is shown in italics.

The synthesized gene constructs hEGF-TF (A) and hEGF-TF (B) were cleaved using Nde I (TaKaRa, Japan) and BamHI (TaKaRa, Japan) restriction enzymes and then were cloned into the pET11a expression vector (Novagen, USA) to construct a recombinant plasmid.

Thereafter, the prepared recombinant plasmid was transformed into *E. coli* BL21 (DE3) to prepare a transformed recombinant microorganism for producing the hEGF-TF fusion protein.

TABLE 1

| Sequence name | Sequence |
|---|---|
| *Bacillus subtilis* xylanase-SP(signal peptide) nucleotide | ATGTTTAAGTTTAAAAAGAATTTCTTAGTTGGATTATCGGCAGCTTTAATGAGTATTAGCT TGTTTTCGGCAACCGCCTCTGCT (SEQ ID NO: 1) |
| codon-optimized SP nucleotide | ATGTTCAAATTCAAAAAAAACTTCCTGGTCGGATTGTCAGCAGCCTTGATGTCTATCTCGC TTTTTAGTGCAACAGCTTCGGCA (SEQ ID NO: 2) |
| human EGF nucleotide | AATAGTGACTCTGAATGTCCCCTGTCCCACGATGGGTACTGCCTCCATGATGGTGTGTGCA TGTATATTGAAGCATTGGACAAGTATGCATGCAACTGTGTTGTTGGCTACATCGGGGAGCG ATGTCAGTACCGAGACCTGAAGTGGTGGGAACTGCGC (SEQ ID NO: 3) |
| codon-optimized human EGF nucleotide | GCCAATTCAGATTCGGAGTGTCCATTATCACACGATGGTTATTGTTTACATGATGGGGTGT GTATGTACATTGAGGCGTTAGACAAATACGCTTGTAATTGTGTGGTCGGCTACATTGGGGA GCGTTGCCAGTACCGTGACTTAAAGTGGTGGGAGCTTCGC (SEQ ID NO: 4) |
| TF nucleotide | ATGCAAGTTTCAGTTGAAACCACTCAAGGCCTTGGCCGCCGTGTAACGATTACTATCGCTG CTGACAGCATCGAGACCGCTGTTAAAAGCGAGCTGGTCAACGTTGCGAAAAAAGTACGTAT TGACGGCTTCCGCAAAGGCAAAGTGCCAATGAATATCGTTGCTCAGCGTTATGGCGCGTCT GTACGCCAGGACGTTCTGGGTGACCTGATGAGCCGTAACTTCATTGACGCCATCATTAAAG AAAAAATCAATCCGGCTGGCGCACCGACTTATGTTCCGGGCGAATACAAGCTGGGTGAAGA CTTCACTTACTCTGTAGAGTTTGAAGTTTATCCGGAAGTTGAACTGCAGGGTCTGGAAGCG ATCGAAGTTGAAAAACCGATCGTTGAAGTGACCGACGCTGACGTTGACGGCATGCTGGATA CTCTGCGTAAACAGCAGGCGACCTGGAAAGAAAAAGACGGCGCTGTTGAAGCAGAAGACCG CGTAACCATCGACTTCACCGGTTCTGTAGACGGCGAAGAGTTCGAAGGCGGTAAAGCGTCT GATTTCGTACTGGCGATGGGCCAGGGTCGTATGATCCCGGGCTTTGAAGACGGTATCAAAG GCCACAAAGCTGGCGAAGAGTTCACCATCGACGTGACCTTCCCGGAAGAATACCACGCAGA AAACCTGAAAGGTAAAGCAGCGAAATTCGCTATCAACCTGAAGAAAGTTGAAGAGCGTGAA CTGCCGGAACTGACTGCAGAATTCATCAAACGTTTCGGCGTTGAAGATGGTTCCGTAGAAG GTCTGCGCGCTGAAGTGCGTAAAAACATGGAGCGCGAGCTGAAGAGCGCCATCCGTAACCG CGTTAAGTCTCAGGCGATCGAAGGTCTGGTAAAAGCTAACGACATCGACGTACCGGCTGCG CTGATCGACAGCGAAATCGACGTTCTGCGTCGCCAGGCTGCACAGCGTITCGGTGGCAACG AAAAACAAGCTCTGGAACTGCCGCGCGAACTGTTCGAAGAACAGGCTAAACGCCGCGTAGT TGTTGGCCTGCTGCTGGGCGAAGTTATCCGCACCAACGAGCTGAAAGCTGACGAAGAGCGC GTGAAAGGCCTGATCGAAGAGATGGCTTCTGCGTACGAAGATCCGAAAGAAGTTATCGAGT TCTACAGCAAAAACAAAGAACTGATGGACAACATGCGCAATGTTGCTCTGGAAGAACAGGC TGTTGAAGCTGTACTGGCGAAAGCGAAAGTGACTGAAAAAGAAACCACTTTCAACGAGCTG ATGAACCAGCAGGCGTAA (SEQ ID NO: 5) |
| hEGF-TF(A) nucleotide | ATGTTCAAATTCAAAAAAAACTTCCTGGTCGGATTGTCAGCAGCCTTGATGTCTATCTCGC TTTTTAGTGCAACAGCTTCGGCAGCCAATTCAGATTCGGAGTGTCCATTATCACACGATGG TTATTGTTTACATGATGGGGTGTGTATGTACATTGAGGCGTTAGACAAATACGCTTGTAAT TGTGTGGTCGGCTACATTGTGGGAGCGTTGCCAGTACCGTGACTTAAAGTGGTGGGAGCTT CGCATGCAAGTTTCAGTTGAAACCACTCAAGGCCTTGGCCGCCGTGTAACGATTACTATCG *CTGCTGACAGCATCGAGACCGCTGTTAAAAGCGAGCTGGTCAACGTTGCGAAAAAAGTACG TATTGACGGCTTCCGCAAAGGCAAAGTGCCAATGAATATCGTTGCTCAGCGTTATGGCGCG TCTGTACGCCAGGACGTTCTGGGTGACCTGATGAGCCGTAACTTCATTGACGCCATCATTA AAGAAAAAATCAATCCGGCTGGCGCACCGACTTATGTTCCGGGCGAATAC4AGCTGGGTGA AGACTTCACTTACTCTGTAGAGTTTGAAGTTTATCCGGAAGTTGAACTGCAGGGTCTGGAA GCGATCGAAGTTGAAAAACCGATCGTTGAAGTGACCGACGCTGACGTTGACGGCATGCTGG ATACTCTGCGTAAACAGCAGGCGACCTGGAAAGAAAAAGACGGCGCTGTTGAAGCAGAAGA CCGCGTAACCATCGACTTCACCGGTTCTGTAGACGGCGAAGAGTTCGAAGGCGGTAAAGCG TCTGATTTCGTACTGGCGATGGGCCAGGGTCGTATGATCCCGGGCTTTGAAGACGGTATCA AAGGCCACAAAGCTGGCGAAGAGTTCACCATCGACGTGACCTTCCCGGAAGAATACCACGC AGAAAACCTGAAAGGTAAAGCAGCGAAATTCGCTATCAACCTGAAGAAAGTTGAAGAGCGT GAACTGCCGGAACTGACTGCAGAATTCATCAAACGTTTCGGCGTTGAAGATGGTTCCGTAG AAGGTCTGCGCGCTGAAGTGCGTAAAAACATGGAGCGCGAGCTGAAGAGCGCCATCCGTAA CCGCGTTAAGTCTCAGGCGATCGAAGGTCTGGTAAAAGCTAACGACATCGACGTACCGGCT GCGCTGATCGACAGCGAAATCGACGTTCTGCGTCGCCAGGCTGCACAGCGTTTCGGTGGCA ACGAAAAACAAGCTCTGGAACTGCCGCGCGAACTGTTCGAAGAACAGGCTAAACGCCGCGT AGTTGTTGGCCTGCTGCTGGGCGAAGTTATCCGCACCAACGAGCTGAAAGCTGACGAAGAG CGCGTGAAAGGCCTGATCGAAGAGATGGCTTCTGCGTACGAAGATCCGAAAGAAGTTATCG AGTTCTACAGCAAAAACAAAGAACTGATGGACAACATGCGCAATGTTGCTCTGGAAGAACA GGCTGTTGAAGCTGTACTGGCGAAAGCGAAAGTGACTGAA4AAGAAACCACTTTCAACGAG CTGATGAACCAGCAGGCGTAA (SEQ ID NO: 6)* |
| hEGF-TF(B) nucleotide | ATGTTCAAATTCAAAAAAAACTTCCTGGTCGGATTGTCAGCAGCCTTGATGTCTATCTCGC TTTTTAGTGCAACAGCTTCGGCAGCCAATTCAGATTCGGAGTGTCCATTATCACACGATGG TTATTGTTTACATGATGGGGTGTGTATGTACATTGAGGCGTTAGACAAATACGCTTGTAAT TGTGTGGTCGGCTACATTGGGGAGCGTTGCCAGTACCGTGACTTAAAGTGGTGGGAGCTTC GCAATGCAAGTTTCAGTTGAAACCACTCAAGGCCTTGGCCGCCGTGTAACGATTACTATC *GCTGCTGACAGCATCGAGACCGCTGTTAAAAGCGAGCTGGTCAACGTTGCGAAAAAAGTAC GTATTGACGGCTTCCGCAAAGGCAAAGTGCCAATGAATATCGTTGCTCAGCGTTATGGCGC GTCTGTACGCCAGGACGTTCTGGGTGACCTGATGAGCCGTAACTTCATTGACGCCATCATT*

TABLE 1-continued

| Sequence name | Sequence |
|---|---|
| | AAAGAAAAAATCAATCCGGCTGGCGCACCGACTTATGTTCCGGGCGAATACAAGCTGGGTG<br>AAGACTTCACTTACTCTGTAGAGTTTGAAGTTTATCCGGAAGTTGAACTGCAGGGTCTGGA<br>AGCGATCGAAGTTGAAAAACCGATCGTTGAAGTGACCGACGCTGACGTTGACGGCATGCTG<br>GATACTCTGCGTAAACAGCAGGCGACCTGGAAAGAAAAAGACGGCGCTGTTGAAGCAGAAG<br>ACCGCGTAACCATCGACTTCACCGGTTCTGTAGACGGCGAAGAGTTCGAAGGCGGTAAAGC<br>GTCTGATTTCGTACTGGCGATGGGCCAGGGTCGTATGATCCCGGGCTTTGAAGACGGTATC<br>AAAGGCCACAAAGCTGGCGAAGAGTTCACCATCGACGTGACCTTCCCGGAAGAATACCACG<br>CAGAAAACCTGAAAGGTAAAGCAGCGAA4TTCGCTATCAACCTGAAGAAAG7TGAAGAGCG<br>TGAACTGCCGGAACTGACTGCAGAATTCATCAAACGTTTCGGCGTTGAAGATGGTTCCGTA<br>GAAGGTCTGCGCGCTGAAGTGCGTAAAAACATGGAGCGCGAGCTGAAGAGCGCCATCCGTA<br>ACCGCGTTAAGTCTCAGGCGATCGAAGGTCTGGTAAAAGCTAACGACATCGACGTACCGGC<br>TGCGCTGATCGACAGCGAAATCGACGTTCTGCGTCGCCAGGCTGCACAGCGTTTCGGTGGC<br>AACGAAAAACAAGCTCTGGAACTGCCGCGCGAACTGTTCGAAGAACAGGCTAAACGCCGCG<br>TAGTTGTTGGCCTGCTGCTGGGCGAAGTTATCCGCACCAACGAGCTGAAAGCTGACGAAGA<br>GCGCGTGAAAGGCCTGATCGAAGAGATGGCTTCTGCGTACGAAGATCCGAAAGAAGTTATC<br>GAGTTCTACAGCAAAAACAAAGAACTGATGGACAACATGCGCAATGTTGCTCTGGAAGAAC<br>AGGCTGTTGAAGCTGTACTGGCGAAAGCGAAAGTGACTGAAAAAGAAACCACTTTCAACGA<br>GCTGATGAACCAGCAGGCGTAA (SEQ ID NO: 7) |
| SP protein | MFKFKKNFLVGLSAALMSISLFSATASA (SEQ ID NO: 8) |
| human EGF<br>protein | NSDSECPLSHDGYCLHDGVCMYIEALDKYACNCVVGYIGERCQYRDLKWWELR<br>(SEQ ID NO: 9) |
| TF protein | MQVSVETTQGLGRRVTITIAADSIETAVKSELVNVAKKVRIDGFRKGKVPMNIVAQRYGAS<br>VRQDVLGDLMSRNFIDAIIKEKINPAGAPTYVPGEYKLGEDFTYSVEFEVYPEVELQGLEA<br>IEVEKPIVEVTDADVDGMLDTLRKQQATWKEKDGAVEAEDRVTIDFTGSVDGEEFEGGKAS<br>DFVLAMGQGRMIPGFEDGIKGHKAGEEFTIDVTFPEEYHAENLKGKAAKFAINLKKVEERE<br>LPELTAEFIKRFGVEDGSVEGLRAEVRKNMERELKSAIRNRVKSQAIEGLVKANDIDVPAA<br>LIDSEIDVLRRQAAQRFGGNEKQALELPRELFEEQAKRRVVVGLLLGEVIRTNELKADEER<br>VKGLIEEMASAYEDPKEVIEFYSKNKELMDNMRNVALEEQAVEAVLAKAKVTEKETTFNEL<br>MNQQA (SEQ ID NO: 10) |
| hEGF-TF<br>protein | MFKFKKNFLVGLSAALMSISLFSATASAANSDSECPLSHDGYCLHDGVCMYIEALDKYACN<br>CVVGYIGERCQYRDLKWWELRMQVSVETTQGLGRRVTITIAADSIETAVTKSELVNVAKKV<br>RIDGFRKGKVPMNIVAQRYGASVRQDVLGDLMSRNFIDAIIKEKINPAGAPTYVPGEYKLG<br>EDFTYSVEFEVYPEVELQGLEAIEVEKPIVEVTDADVDGMLDTLRKQQATRKEKDGAVEAE<br>DRVTIDFTGSVDGEEFEGGKASDFVLAMGQGRMIPGFEDGIKGHKAGEEFTIDVTFPEEYH<br>AENLKGKAAKFAINLKKVEERELPELTAEFIKRFGVEDGSVEGLRAEVRKNMERELKSAIR<br>NRVKSQAIEGLVKANDIDVPAALIDSEIDVLRRQAAQRFGGNEKQALELPRELFEEQAKRR<br>VVVGLLLGEVIRTNELKADEERYKGLIEEMASAYEDPKEVIEFYSKNKELMDNMRNVALEE<br>QAVEAVLAKAKVTEKETTFNELMNQQA (SEQ ID NO: 11) |

Example 2. Confirmation of Expression Induction of hEGF-TF Fusion Protein of the Present Invention and its Secretion into the Culture Medium The present inventors have confirmed whether the transformed *E. coli* BL21 (DE3) prepared in Example 1 actually produced hEGF-TF fusion protein (hEGF-TF).

First, the transformed *E. coli* BL21 (DE3) prepared in Example 1 was inoculated into 5 mL of LB medium (1% tryptophan, 1% sodium chloride, and 0.5% yeast extract) containing ampicillin. Shaking culture was performed at 37° C. After culturing in 500 mL of the same medium so that the absorbance became 0.8 at 600 nm, IPTG (Isopropyl-β-D-thiolgalactoside) was added to a final concentration of 0.01 mM to induce protein expression at 20° C. In the process of inducing protein expression, 1 ml of samples were collected for each time period (0 hours, 12 hours, 24 hours, 48 hours, and 96 hours), and the cells and the culture medium were separated at 4° C. and 8,000 rpm, respectively. After the cells were completely suspended in distilled water, the cells were disrupted using a sonicator and a solution containing cellular proteins was separated.

In order to check whether the expressed proteins were discharged into the culture medium for each time, the proteins were confirmed by SDS-PAGE using the solutions and the culture solutions containing the separated cellular proteins as samples.

The amount of cellular protein and the protein secreted into the culture medium according to time after the hEGF-TF (A) construct was inserted into *E. coli* BL21 (DE3) is shown in FIG. 2A; and the amount of cellular protein and the protein secreted into the culture medium according to time after the hEGF-TF (B) construct was inserted into *E. coli* BL21 (DE3) is shown in FIG. 3A.

As a result, as shown in FIGS. 2A and 3A, it was interestingly confirmed that when protein expression was induced using a construct composed of hEGF-TF (B), that is, TA sequence was inserted between the hEGF gene and the TF gene, the production and secretion amount in the culture medium of the final product, hEGF-TF protein, was significantly increased, compared to the hEGF-TF (A) construct in which TA sequence was not inserted.

Example 3. Confirmation of Optimal Conditions for Increasing the Production (Secretion Amount) of the hEGF-TF Fusion Protein of the Present Invention In order to establish optimal conditions for increasing the production (secretion amount) of the hEGF-TF fusion protein, the present inventors have measured the secretion level of the hEGF-TF fusion protein by applying conditions according to high-concentration culture and medium replacement of recombinant microorganisms prior to induction of expression.

The transformed *E. coli* BL21 (DE3) prepared in Example 1 was inoculated into 5 mL of LB medium (1% tryptophan, 1% sodium chloride, and 0.5% yeast extract) containing ampicillin. Shaking culture was performed at 37° C. After culturing in 500 mL of the same medium so that the absorbance became 2.5 at 600 nm, centrifugation was performed at 4° C. and 8,000 rpm for 10 minutes. Then, the culture medium was discarded and the precipitated cells were suspended in the same amount of medium, and then IPTG (Isopropyl-β-D-thiolgalactoside) was added to a final concentration of 0.01 mM to induce gene expression. Thereafter, while cultured at 20° C., cells and culture medium were separated at 4° C. and 8,000 rpm for 12 hours, 24 hours, 48 hours, and 96 hours, respectively. After the cells were completely suspended in distilled water, the cells were disrupted using a sonicator, and a solution containing cellular proteins was separated.

In order to check whether the expressed proteins are discharged into the culture medium, the solutions and the culture medium containing cellular proteins separated at 12 hours, 24 hours, 48 hours, and 96 hours, respectively, were used as samples, and the protein is confirmed by SDS-PAGE.

The amount of cellular protein and the protein secreted into the culture medium according to time after the hEGF-TF (A) construct was inserted into *E. coli* BL21 (DE3) is shown in FIG. 2B; and the amount of cellular protein and the protein secreted into the culture medium according to time after the hEGF-TF (B) construct was inserted into *E. coli* BL21 (DE3) is shown in FIG. 3B.

As a result, as shown in FIG. 3B, it was confirmed that at 96 hours of culture, 1300.6 mg of hEGF-TF per liter of culture was secreted, which was significantly increased by nearly 30% compared to the result of FIG. 3A in Example 2, in which 1087.6 mg of hEGF-TF per 1 liter of culture was discharged at 96 hours of culture.

This suggests that the secretion of hEGF-TF protein may be excellently improved when the medium is replaced while culturing the transformed microorganism at a high concentration before induction of expression.

That is, optimal conditions for increasing hEGF-TF fusion protein output have been established by demonstrating that the present invention shows a synergistic effect of increasing the secretion of an hEGF-TF fusion protein according to high-concentration culture and medium replacement conditions of recombinant microorganisms before induction of expression.

Therefore, it may be usefully used for mass production of high-quality human epidermal growth factor (EGF)-*E. coli*-derived trigger factor (TF) fusion protein.

Accordingly, the following examples were performed by using hEGF-TF, which was produced by introducing the hEGF-TF (B) construct in which the TA sequence was inserted between the hEGF gene and the TF gene.

Example 4. Quantitative Analysis of hEGF-TF Fusion Protein of the Present Invention In order to check the amount of hEGF-TF fusion protein secreted into the culture medium, the present inventors have loaded 1, 4, and 8 μg of standard protein onto an SDS-PAGE gel, and created a calibration curve using the ImageJ program. The amount of protein corresponding to the epidermal growth factor-trigger factor fusion protein band among the proteins secreted into the culture medium in Example 3-3 was confirmed.

As a result, as shown in Table 2 below, it was confirmed that the amount of secreted protein was increased according to the culture time when the hEGF-TF protein secreted for each time period of FIG. 3B was quantitatively analyzed.

TABLE 2

| Culture time | 12 h | 24 h | 48 h | 96 h |
|---|---|---|---|---|
| Amount of epidermal growth factor-Trigger factor (mg/L) | 0 | 139.2 | 1171.1 | 1300.6 |

Example 5. Purification and Confirmation of hEGF-TF Fusion Protein of the Present Invention For the purification of hEGF-TF fusion protein, the present inventors have inoculated *E. coli* BL21 (DE3) containing hEGF-TF (B) construct in 5 mL of LB broth (1% tryptophan, 1% sodium chloride, and 0.5% yeast extract) containing ampicillin. The shaking culture was performed at 37° C. This was again cultured in 1 L of the same medium so that the absorbance became 0.8 at 600 nm, and then IPTG was added to be 0.01 mM, and protein expression was induced at 20° C. for 24 hours. The culture medium was centrifuged at 4° C. and 8,000 rpm for 10 minutes to collect only the precipitated cells. The collected cells were purified by osmotic pressure by adding FO solution (3% NaCl) after cryopreservation.

As a result, as shown in FIG. 4, the protein was identified using SDS-PAGE, and the hEGF-TF fusion protein was confirmed by performing western blotting using the trigger factor antibody protein.

Example 6. Cell Regeneration Effect of hEGF-TF Fusion Protein of the Present Invention In order to evaluate the effect of the hEGF-TF fusion protein of the present invention on human dermal fibroblast (HDF) proliferation, the present inventors have measured cell growth and viability using an MTT assay.

First, DMEM/F12 (3:1) mixed medium containing 10% FBS was used for culturing HDF cells, and HDF cells were inoculated in a 96-well plate in $1 \times 10^3$ cells/well, and at the same time, samples were treated with 0 ng/μl (control), 0.1 ng/μl, 1 ng/μl, and 10 ng/μl hEGF-TF fusion protein, respectively. Then, they were cultured at 37° C. and 5% $CO_2$ for 1 day and 3 days, respectively. At this time, as an experimental comparison group, an experiment was performed under the same concentration and conditions using commercially available hEGF (Sigma-Aldrich). After the culture was completed, the MTT solution was added. They were cultured for 4 hours, and then the medium was removed. DMSO was added thereto, and the absorbance was measured at 450 nm.

Cell growth rates are calculated as follows:

$$\text{Cell growth rate (\%)} = ((\text{absorbance of experimental group} - \text{absorbance of control group})/\text{absorbance of control group}) \times 100.$$

As a result, as shown in FIG. 5, in the experimental group in which HDF cells were treated with 0.1 ng/μl of the hEGF-TF fusion protein of the present invention, the cell growth rate was increased to 4.8% on the 1st day and 57.5% on the 3rd day compared to the control group; in the experimental group treated with 1 ng/μl, the cell growth rate was increased to 10.6% on the 1st day and 73% on the 3rd day compared to the control group. In addition, in the experimental group treated with 10 ng/μl, the cell growth rate was increased to 50.7% on the 1st day and 84.9% on the 3rd day compared to the control group.

This demonstrates that the hEGF-TF fusion protein of the present invention exhibits excellently increased cell growth efficacy compared to the commercially available hEGF as a control group.

Example 7. Wound Healing Effect of hEGF-TF Fusion Protein of the Present Invention The present inventors have evaluated the wound healing efficacy of the hEGF-TF fusion protein of the present invention on human fibroblasts.

First, 70 μl of fibroblasts ($5 \times 10^5$ cells/ml) were inoculated into a culture-insert culture dish (ibidi), and 24 hours later, the culture-insert was removed. They were treated with hEGF-TF at a concentration of 0 ng/μl (control), 0.1 ng/μl, and 1 ng/μl, respectively. At this time, an experiment was performed under the same concentration and conditions using commercially available hEGF (Sigma-Aldrich) as an experimental comparative group. Cell images at 3, 6, 9, 12, and 24 hours of culture were analyzed using the imageJ program to confirm the wound healing efficacy.

As a result, as shown in FIG. 6, the experimental group treated with 1 ng/μl of the hEGF-TF fusion protein of the present invention showed a higher wound healing effect as compared to the control group and the comparative group (commercially available hEGF) in general.

This demonstrates that the hEGF-TF fusion protein of the present invention exhibits excellently increased wound healing efficacy compared to the commercially available hEGF as a control group.

Overall, the novel human epidermal growth factor (hEGF)-trigger factor (TF) fusion protein of the present invention produced by a construct in which a signal peptide gene is bound to the hEGF gene according to the present invention and a TA sequence is inserted between the hEGF gene and the TF gene improves the function of secreting the hEGF-TF fusion protein into the culture medium, that is, the function of producing in *E. coli* and secreting excess extracellularly so that thus the production capacity thereof is improved, and cell growth and wound healing efficacy thereof is excellent compared to that of commercially available hEGF. Therefore, it is widely used as an active ingredient for a cosmedical composition and a pharmaceutical composition for external application to skin.

Further, in the method according to the present invention, optimal conditions have been established to improve the production efficiency of the human epidermal growth factor, and thus human epidermal growth factor may be obtained in high yield so that it may be usefully applied to mass production.

As described above in detail a specific part of the content of the present invention, it will be obvious for those of ordinary skill in the art that this specific description is only a preferred embodiment, and the scope of the present invention is not limited thereby. Accordingly, it is intended that the substantial scope of the present invention be defined by the appended claims and their equivalents.

---

---

The invention claimed is:

1. A human epidermal growth factor (hEGF)-trigger factor (TF) fusion protein consisting of the amino acid sequence of SEQ ID NO: 11.

2. A method for producing the hEGF-TF fusion protein of claim 1, the method comprising steps of:
   (a) preparing a recombinant expression vector comprising a nucleic acid construct comprising a nucleotide sequence encoding the hEGF-TF fusion protein of claim 1;
   (b) preparing a transformant by introducing the recombinant expression vector of the step (a) into a microorganism; and
   (c) culturing the transformant of the step (b) to produce the hEGF-TF fusion protein.

3. The method of claim 2, wherein the step (c) further comprises step of culturing the transformant and replacing the medium before producing the hEGF-TF fusion protein.

4. A method for treating a skin disease, the method comprising administering a composition comprising the hEGF-TF fusion protein of claim 1 to a subject having the skin disease.

5. The method of claim 4, wherein the composition is a pharmaceutical composition for treating a skin disease.

6. The method of claim 4, wherein the composition is a food composition for treating a skin disease.

7. The method of claim 4, wherein the composition is a cosmetic composition for treating a skin disease.

\* \* \* \* \*